United States Patent
Stupp et al.

(10) Patent No.: US 9,904,659 B1
(45) Date of Patent: *Feb. 27, 2018

(54) TECHNIQUE FOR IDENTIFYING ASSOCIATION VARIABLES

(71) Applicant: Trigeminal Solutions, Inc., San Carlos, CA (US)

(72) Inventors: Steven Elliot Stupp, San Carlos, CA (US); Chris Carpenter, Sunnyvale, CA (US)

(73) Assignee: Trigeminal Solutions, Inc., San Carlos, CA (US)

( * ) Notice: Subject to any disclaimer, the term of this patent is extended or adjusted under 35 U.S.C. 154(b) by 580 days.

This patent is subject to a terminal disclaimer.

(21) Appl. No.: 13/573,888

(22) Filed: Oct. 11, 2012

Related U.S. Application Data

(66) Substitute for application No. 61/627,606, filed on Oct. 14, 2011.

(51) Int. Cl.
| | | |
|---|---|---|
| *G06F 19/10* | (2011.01) | |
| *G06F 17/18* | (2006.01) | |
| *G06F 19/24* | (2011.01) | |
| *G06F 19/18* | (2011.01) | |

(52) U.S. Cl.
CPC .............. *G06F 17/18* (2013.01); *G06F 19/24* (2013.01); *G06F 19/10* (2013.01); *G06F 19/18* (2013.01)

(58) Field of Classification Search
None
See application file for complete search history.

(56) References Cited

U.S. PATENT DOCUMENTS

| | | | | |
|---|---|---|---|---|
| 7,311,666 B2* | 12/2007 | Stupp et al. | .................. | 600/300 |
| 8,639,446 B1 | 1/2014 | Stupp | .............................. | 702/19 |
| 2013/0261490 A1* | 10/2013 | Truccolo et al. | ............. | 600/544 |

OTHER PUBLICATIONS

McLachlan et al. (Bioinformatics (2006) vol. 22, pp. 1608-1615).*
Zhai et al. (Journal of Computational Biology (2010) vol. 17, pp. 581-592).*

* cited by examiner

*Primary Examiner* — Lori A. Clow
(74) *Attorney, Agent, or Firm* — Steven Stupp

(57) ABSTRACT

An apparatus determines patterns of occurrence of compound variables based on a set of mathematical interactions and patterns of occurrence of a set of electrical signals. Then, the apparatus calculates statistical relationships corresponding to a pattern of occurrence of neural activity of one or more organisms and the patterns of occurrence of the compound variables. Moreover, the apparatus determines numbers of occurrences of electrical signals that were used to determine compound variables in at least a statistically significant subset of the compound variables, and determines numbers of different mathematical interactions that were used to determine the compound variables in the subset for the electrical signals that are associated with the corresponding numbers of occurrences. Next, the apparatus identifies one or more of the electrical signals as one or more association variables based on the numbers of occurrences and/or the numbers of different mathematical interactions.

23 Claims, 12 Drawing Sheets

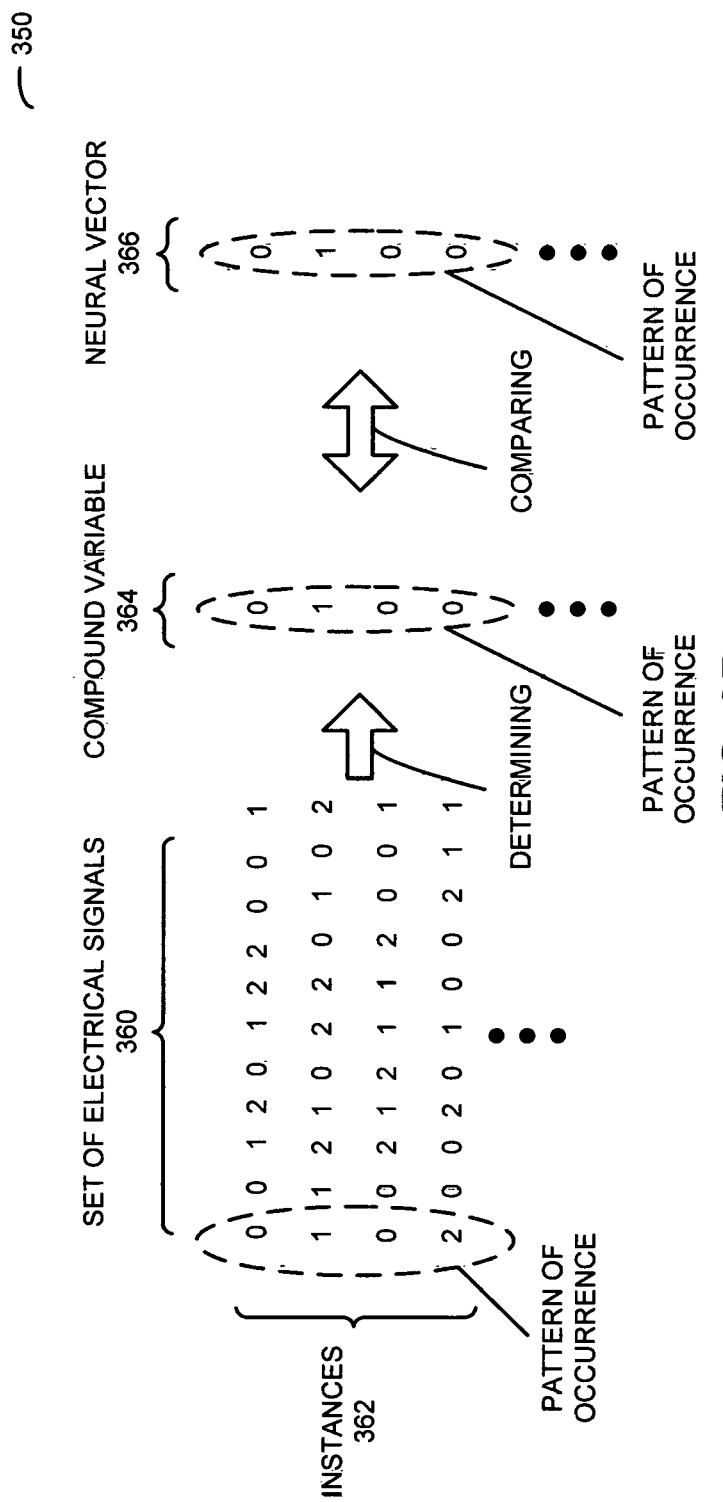

TECHNIQUE FOR IDENTIFYING ASSOCIATION VARIABLES

CROSS REFERENCE TO RELATED APPLICATIONS

This application claims priority under 35 U.S.C. 119(e) to U.S. Provisional Application Ser. No. 61/627,606, "Technique for Identifying Association Variables," filed on Oct. 14, 2011, the contents of which are herein incorporated by reference.

FIELD

The present disclosure relates generally to an apparatus, and related methods, for processing data, and more specifically, for identifying association variables, such as electrical signals, which are associated with the activity of neural circuits.

BACKGROUND

Many mathematical problems involve analyzing data to determine relationships between variables. For example, in regression analysis an expression can be determined to describe data (which is sometimes referred to as 'fitting' the expression to the data). This is shown in FIG. 1A, which presents a drawing 100 illustrating the fitting a line to data. The equation for a line y (the independent variable) can be expressed as $$y=mx+b,$$

where x (the data) is the dependent variable, and m and b are unknown coefficients (the slope and y-intercept, respectively) that are to be determined during the fitting. In this example, each datum in the data corresponds to a point in the x-y plane (such as $x_0$, $y_0$).

Typically, the minimum number of data points needed to uniquely determine the fitting equation equals the number of unknowns in the fitting equation (as shown in FIG. 1A, for a line, the minimum number of data points is two). If there are more data points than this minimum number, statistical techniques such as least-squares regression may be used to determine the unknown coefficients. However, if there are fewer data points available than the minimum number, it is typically not possible to uniquely determine the unknowns. This is shown in FIG. 1B, which presents a drawing 150 illustrating the fitting of multiple lines to a datum. In principle, there are an infinite number of equivalent fitting solutions that can be determined. This type of problem is sometimes referred to as 'sparse' or 'underdetermined.'

Unfortunately, many interesting problems are underdetermined. For example, in biology, there are important differences in the central nervous systems within a species (i.e., from individual to individual) and between species. These differences in the central nervous system reflect underlying variations in the neurons and the neural circuits that contain them. Collectively, the neurons and their interconnections in an organism constitute its neurome, and these neurons can be identified and represented by their properties.

One approach for characterizing the properties of the neurons in an organism is to measure electrical signals associated with the activity of the neurons using electrodes. In principle, the measured electrical signals include valuable information about the organism's central nervous system. In practice, there are often an enormous number of electrical signals and a much smaller number of observations (such as repeated cycles of a particular activity). As a consequence, the problem is underdetermined, and it can be difficult to identify a subset of the electrical signals that are relevant to the particular activity without an excessive number of false positives. These false positives can significantly increase the time and expense needed to analyze the electrical signals to identify the subset.

Therefore, there is a need for an analysis technique to identify associations in underdetermined problems without the problems listed above.

SUMMARY

One embodiment of the present disclosure describes an apparatus, such as a computer system or a circuit, to identify one or more association variables that are associated with neural activity. This apparatus may determine patterns of occurrence of compound variables based on a set of mathematical interactions and patterns of occurrence of a set of electrical signals which are associated with corresponding electrodes and which are measured for one or more organisms (such as humans, animals, bacteria, fungi and/or plants), where a pattern of occurrence of a given compound variable may be determined based on a given mathematical interaction in the set of mathematical interactions and patterns of occurrence of a given pair of electrical signals in the set of electrical signals. Moreover, the apparatus may calculate statistical relationships corresponding to a pattern of occurrence of the neural activity in the one or more organisms and the patterns of occurrence of the compound variables. Note that a given statistical relationship corresponds to the pattern of occurrence of the neural activity in the one or more organisms and a pattern of occurrence of a given compound variable, and the calculation may include contributions from presence and absence information in the patterns of occurrence of the neural activity and the pattern of occurrence of the given compound variable.

Using the statistical relationships, the apparatus may determine numbers of occurrences of electrical signals that were used to determine the compound variables in at least a subset of the compound variables, where the subset of the compound variables have statistical relationships greater than a statistical confidence value. Furthermore, the apparatus may determine numbers of different mathematical interactions used to determine the compound variables in the subset for the electrical signals that are associated with the corresponding numbers of occurrences. Then, the apparatus may identify one or more of the electrical signals in the set of electrical signals as the one or more association variables based on the numbers of occurrences and/or the numbers of different mathematical interactions.

In some embodiments, the given compound variable is determined by performing a mathematical operation specified by the given mathematical interaction on corresponding entries in a pattern of occurrence of a first electrical signal in the given pair of electrical signals and a pattern of occurrence of the second electrical signal in the given pair of electrical signals.

Moreover, the calculating may involve a non-parametric statistical analysis technique, such as: a chi-square analysis technique, a log-likelihood ratio analysis technique, a goodness-of-fit (G-test) technique, and/or a Fisher's exact probability analysis technique. More generally, the calculating may involve a supervised learning technique. This supervised learning technique may include a support vector machines (SVM) analysis technique and/or a classification and regression tree (CART) analysis technique.

Note that the statistical confidence value may correspond to a statistical significance value associated with the statistical relationships. For example, the statistical confidence value may correspond to a noise floor in the statistical relationships. This noise floor may be determined based on approximate stability of at least a portion of a ranking of the electrical signals based on the number of occurrences. Moreover, the approximate stability may be for statistical confidence values between the statistical confidence value and another statistical confidence value, where the other statistical confidence value corresponds to a larger statistical significance value associated with the statistical relationships than the statistical confidence value.

In some embodiments, the apparatus calculates additional statistical relationships corresponding to a pattern of occurrence of a sequence of values and the patterns of occurrence of the compound variables, where a given additional statistical relationship corresponds to the pattern of occurrence of the sequence of values and the pattern of occurrence of the given compound variable. This calculation may include contributions from presence and absence information in the patterns of occurrence of the sequence of values and the pattern of occurrence of the given compound variable. Then, the apparatus determines additional numbers of occurrences of electrical signals that were used to determine additional compound variables in at least another subset of the compound variables, where the other subset have statistical relationships greater than the statistical confidence value or another statistical confidence value. Moreover, the apparatus may correct the numbers of occurrences based on the additional numbers of occurrences prior to identifying the one or more association variables. Note that the sequence of values may include a random or a pseudo-random sequence of values, and a number of entries in the sequence of values may equal a number of repetitions of the neural activity.

The number of entries in the pattern of occurrence of the neural activity may equal a number of repetitions of the neural activity by the one or more organisms. Moreover, the set of electrical signals may include average values within time intervals proximate to the neural activity (i.e., before or after the neural activity). In some embodiments, the set of electrical signals includes ternary encoded samples of the electrical signals measured using the electrodes.

Furthermore, a given pattern of occurrence of a given variable, which can include the neural activity, the given compound variable, or either one of the given pair of electrical signals, may include presence and absence information of the given variable.

In some embodiments, the apparatus excludes at least some of the compound variables prior to calculating the statistical relationships. Note that a given excluded compound variable may have a number of presences or absences in the pattern of occurrence of the given excluded compound variable that is greater than a first value or less than a second value.

The apparatus may resample the set of electrical signals prior to determining the patterns of occurrence of the compound variables. Additionally, the apparatus may exclude at least some of the electrical signals in the set of electrical signals prior to calculating the compound variables. Note that a given excluded electrical signal may have a number of presences or absences in the pattern of occurrence of the given excluded electrical signal that is greater than a third value or less than a fourth value.

Note that the neural activity may correspond to a physical or mental activity performed by the organism. Furthermore, the electrical signals in the set of electrical signals may correspond to brainwave data or neurological stimulation.

Note that identifying the one or more association variables constitutes an underdetermined problem. For example, the number of entries in the pattern of occurrence of the neural activity may be significantly less than a number of electrical signals in the set of electrical signals.

Another embodiment provides a method that includes at least some of the operations performed by the apparatus or an electronic device.

Another embodiment provides a computer-program product for use with the apparatus. This computer-program product includes instructions for at least some of the operations performed by the apparatus.

BRIEF DESCRIPTION OF THE DRAWINGS

FIG. 3B is a drawing illustrating identifying one or more association variables that are associated with a neural activity in accordance with an embodiment of the present disclosure.

Figure 1A:
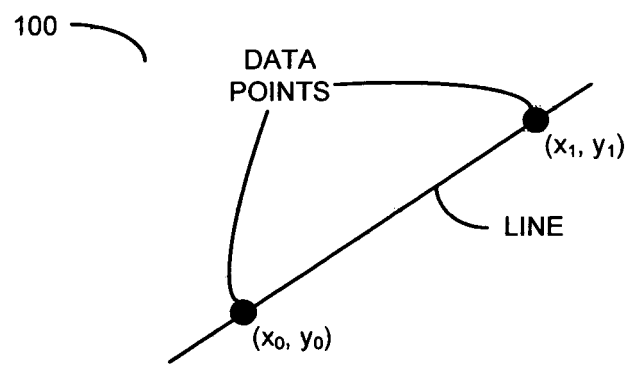
FIG. 1A is a drawing illustrating fitting a line to data.
Figure 1B:
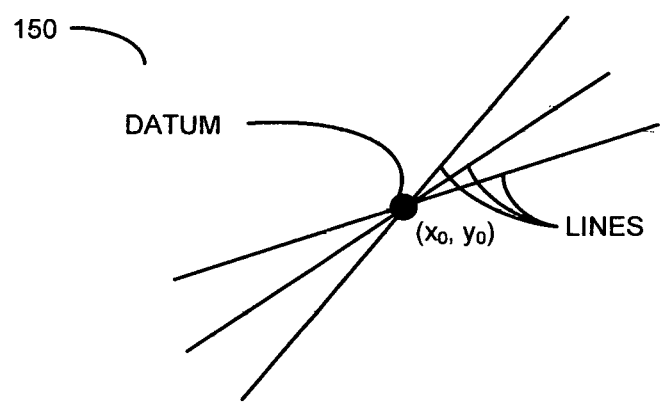
FIG. 1B is a drawing illustrating fitting multiple lines to a datum.

Table 1 provides a contingency table in an exemplary embodiment.

Note that like reference numerals refer to corresponding parts throughout the drawings. Moreover, multiple instances of the same part are designated by a common prefix separated from an instance number by a dash.

DETAILED DESCRIPTION

Embodiments of an apparatus (such as a computer system or a circuit), a method (which is sometimes referred to as an 'identification technique'), and a computer-program product (e.g., software) for use with the apparatus are described. This apparatus may be used to identify one or more association variables that are associated with a neural activity. In particular, based on a set of mathematical interactions compound variables may be determined for electrical signals in a set of electrical signals, which are associated with corresponding electrodes and which are measured for one or more organisms (such as humans, animals, bacteria, fungi and/or plants). (Alternatively, the compound variables may be pre-determined.) A given compound variable may be determined using a given mathematical interaction and one or more electrical signals (such as a given pair of electrical signals), where a given entry in the compound variable is based on a presence or absence of the one or more electrical signals during or proximate to (such as before or after) an instance or repetition of the neural activity for a given one of the organisms. For example, the given entry may be determined by performing a logical operation (AND, OR, NOT, XOR and/or another Boolean operation) or a mathematical operation specified by the given mathematical interaction on the values of the one or more electrical signals.

Then, the apparatus may calculate statistical relationships between a pattern of occurrence of the neural activity in the one or more organisms (e.g., presence or absence of the neural activity in the one or more organisms) with patterns of occurrence of compound variables in the set of electrical signals (e.g., presence or absence entries in the compound variables). These calculations may involve a non-parametric statistical analysis technique and/or a supervised learning technique.

Next, the apparatus may determine numbers of occurrences of electrical signals that were used to determine compound variables in at least a subset of the compound variables that have statistical relationships greater than a statistical significance value, which may correspond to a noise floor in the statistical relationships. This noise floor may be determined based on approximate stability of at least a portion of an occurrence ranking based on the numbers of occurrences for statistical confidence values between the statistical confidence value and another statistical confidence value, i.e., a range of statistical confidence values.

Moreover, the apparatus may determine numbers of different mathematical interactions that were used to determine the compound variables in the subset of the compound variables for the electrical signals that are associated with the corresponding numbers of occurrences.

Furthermore, the apparatus may identify one or more of the electrical signals as one or more association variables based on the numbers of occurrences and/or the numbers of different mathematical interactions. For example, N association variables may be the top-N values in rankings based on the numbers of occurrences and/or the numbers of different mathematical interactions.

In some embodiments, the apparatus performs a correction for a background prior to identifying the one or more association variables. For example, the apparatus may subtract from the occurrence ranking another occurrence ranking which is associated with numbers of occurrences of the electrical signals that were used to determine compound variables in other statistically significant statistical relationships (i.e., those compound variables which have statistical relationship values greater than the same or another statistical significance value) between the patterns of occurrence of the compound variables and a pattern of occurrence of a sequence of values (such as a random or a pseudo-random sequence of values).

In the discussion that follows, the following definitions are used:

the meaning of 'configured' may include 'to set up for operation especially in a particular way', such as a circuit configured, for a particular function or a program configured to be executed on a particular processor or computer;

the meaning of 'configurable' may include 'capable of being configured in a particular way', such as a programmable circuit that is configurable or a program (source code or compiled) that can be configured to executed on the particular processor at run time (in this disclosure, configured and configurable are considered to have meanings that encompass each other and may be used interchangeably);

the meaning of 'based on' may include 'is a function of', 'using' and/or 'according to';

the meaning of 'organisms' may include 'a group that includes one or more people, animals, bacteria, fungi, plants and/or an engineered life form (such as a genetically engineered life form);

the meaning of 'pattern of occurrence of a variable or a neural activity for one or more organisms' may include 'values corresponding to presence and/or absence information for the variable or the neural activity in one or more instances or repetitions of the neural activity for one or more of the organisms.

the meaning of 'ranking' may include 'a listing of items in a group according to a system of rating';

the meaning of 'disease' may include 'an illness or sickness characterized by an impairment of health or a condition of abnormal functioning'.

In general, the neural activity is associated with a physical and/or a mental activity of the one or more organisms. This neural activity may be associated with a disease, such as: a type of cancer, an auto-immune disease, an immune-related disease, a form of arthritis, a disease of at least a portion of the endocrine system, a metabolic disease, cardiovascular disease, a neurological disease, a respiratory disease, joint disease, gastrointestinal disease, a disease of a component in blood, a psychological disease or mental illness, asthma, an allergy, an inflammatory disease, a disease involving a histamine response, a type of skin disease, a circadian rhythm disorder a degenerative disease, a chronic disease, and/or an episodic disease. For example, the disease may include: rheumatoid arthritis, lupus, thyroid disease, gout, diabetes, chronic fatigue syndrome, insomnia, depression, anxiety, bipolar disorder, colitis, ulcerative colitis, inflammatory bowel disease, Crohn's disease, candida, celiac disease, hepatitis, irritable bowel syndrome, one or more food allergies, one or more food sensitivities, menstrual cramps, chronic pain, back pain, facial pain, fibromyalgia, asthma, migraines, abdominal migraines, cyclic vomiting syndrome, cluster headaches, chronic headaches, tension headaches, another type of headaches, seizures, epilepsy, neurodermatitis, acne, psoriasis, adiposity, hypertonia, heart disease, hypertension, arteriosclerosis, and/or acquired immune deficiency syndrome. In some embodiments, the disease may include multiple illnesses, which may or may not have an associated comorbidity. However, in some embodiments the neural activity is associated with a learned behavior (such as a golf swing) or, more generally, a characteristic, such as: intelligence, a physical attribute, a skill, memory, longevity, etc. Thus, the neural activity may not be confided to a disease; instead it may include a positive or desirable attribute.

We now describe embodiments of a technique for identifying one or more association variables that are associated with a neural activity. In the discussion that follows, electrical signals associated with brainwaves or brain electrical activity, such as electroencephalography (EEG) signals, are used as an illustration of the set of electrical signals. However, in other embodiments the electrical signals may be associated with the action potential of nerve cells (or neurons) that are external to the central nervous system or other electrical signals associated with one or more organisms. Moreover, the electrical signals may be measured using a variety of techniques (including: patch clamps, superconducting quantum interference devices, electrocardiogram, electromyogram, etc.), as well as techniques that correspond to the electrical signals, such as optical imaging of an optical dye, etc.

Furthermore, in some embodiments the statistical associations of the set of electrical signals with the neural activity are analyzed in conjunction with other variables (i.e., statistical associations are also determined between the neural activity and the other variables). For example, the other variables may include expression or suppression of genetic information in the one or more organisms, such as: epigenetic information (such as methylation or demethylation), information associated with DNA (such as one or more copy number variations or frame shifts), information associated with ribonucleic acid (RNA), information associated with one or more proteins (such as one or more enzymes), and/or information associated with another biological marker or type of biological marker. Additionally, the other variables may include environmental factors, such as: environmental stimuli (for example, light or sound), weather conditions, behaviors, patterns of behaviors (when the behaviors occur or do not occur), diet (including foods or beverages consumed or not consumed), dietary patterns (when the foods or beverages are consumed or are not consumed), use of drugs (prescription or recreational), activities, exposure to chemicals, exposure to toxins, exposure to one or more fungi, and/or exposure to infections agents (for example, bacteria, viruses, fungi, and/or prions).

Figure 2A:
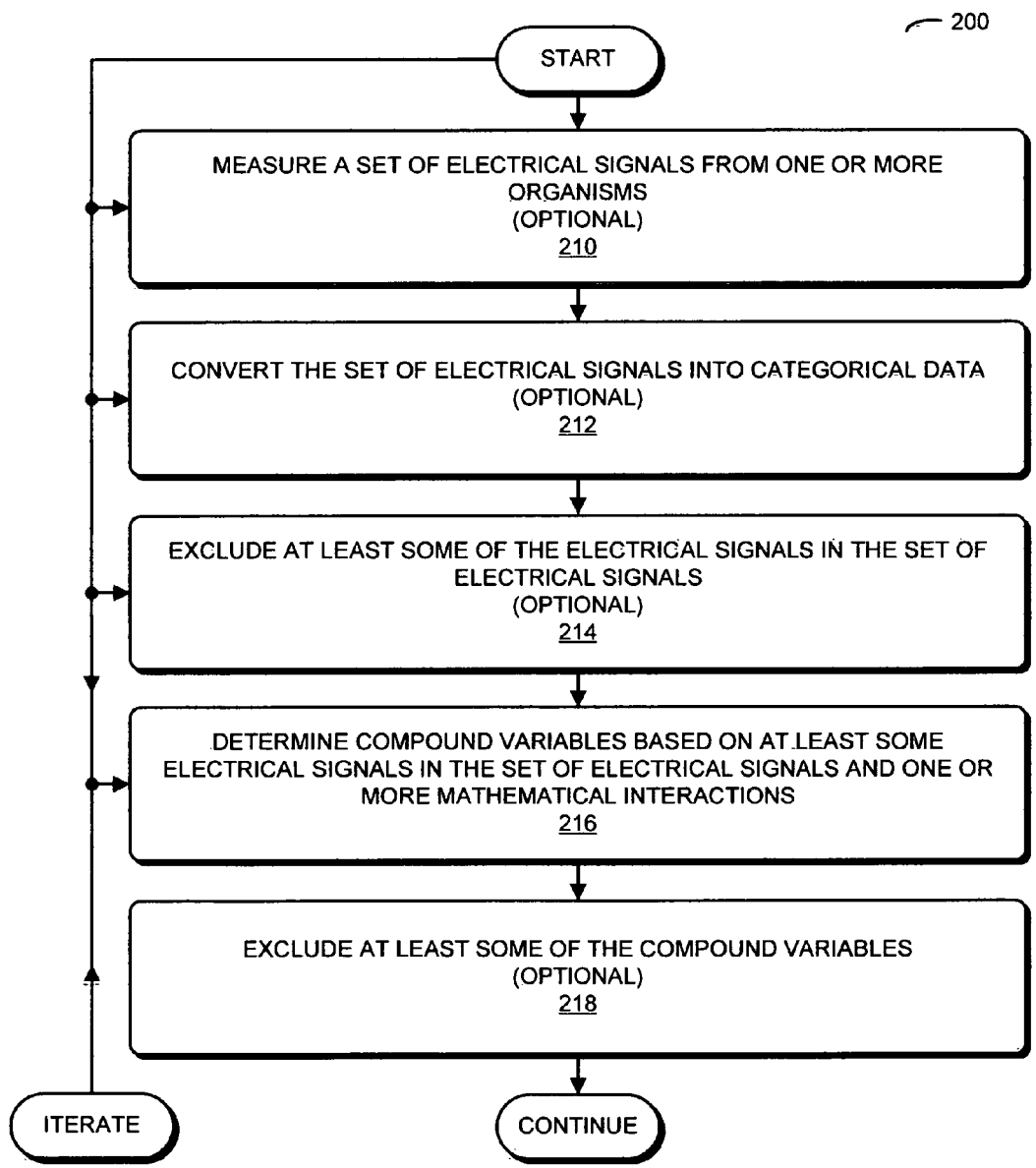
FIG. 2A is a flow chart illustrating a process for identifying one or more association variables that are associated with a neural activity in accordance with an embodiment of the present disclosure.
Figure 7:
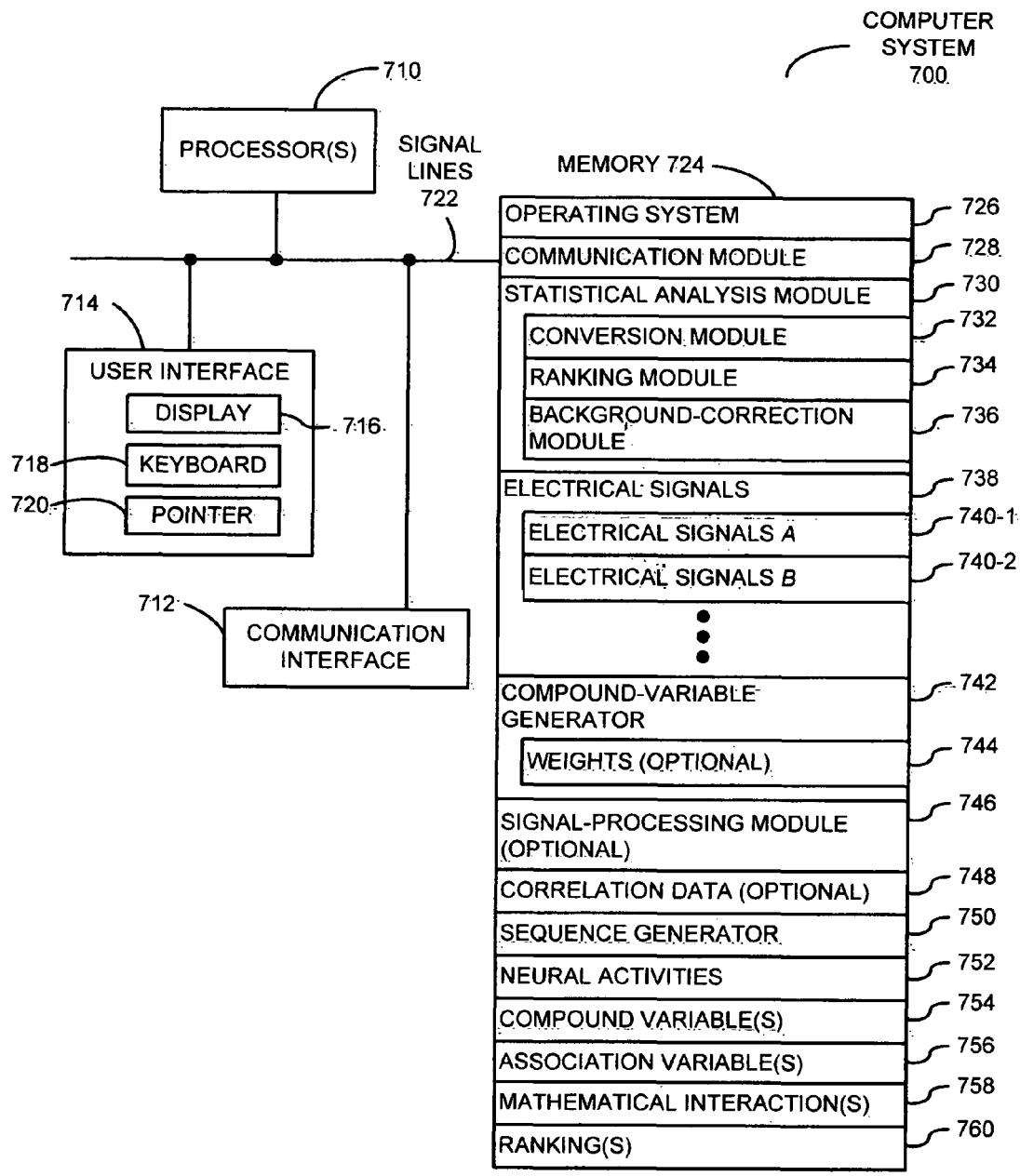
FIG. 7 is a block diagram illustrating a computer system in accordance with an embodiment of the present disclosure.

FIG. 2A presents a flow chart illustrating a process 200 for identifying one or more association variables that are associated with a neural activity, which may be performed by a computer system (such as computer system 700 in FIG. 7). During this process, a set of electrical signals are optionally measured from one or more organisms (operation 210). For example, the set of electrical signals may be measured from the one or more organisms while the one or more organisms perform one or more instances or repetitions of the neural activity using electrodes.

Then, the set of electrical signals may be optionally converted into categorical data (operation 212). For example, analog electrical signals (such as EEG signals) may be sampled during or proximate to one or more instances or repetitions of the neural activity. In an exemplary embodiment, the electrical signals are represented by ternary values, such as {0, 1 or 2}, for electrical signals during time intervals proximate to the neural activity that are, respectively, below a first threshold, between the first threshold and a second threshold, and above the second threshold. However, other encoding techniques may be used with fewer or more thresholds. Furthermore, different thresholds may be used for different electrical signals and/or for the other variables.

Next, at least some of the electrical in the set of electrical signals may be optionally excluded (operation 214) prior to determining compound variables based on at least some of the electrical signals in the set of electrical signals (operation 216) (or a remainder of the set of electrical signals after the optional excluding in operation 214) and one or more mathematical interactions. For example, a given excluded electrical signals may have a number of presence or absences in a pattern of occurrence in the set of electrical signals (i.e., in the data determined from the one or more organisms using the electrodes) which is greater than a first value or less than a second value. This may exclude electrical signals that have too few or too many presences or absences for there to be a statistically significant relationship with a pattern of occurrence of the neural activity. For these excluded electrical signals, it may not be possible to determine whether or not there is a relationship with the neural activity. In an exemplary embodiment, the first value is 5, 10 or 15% presence or absence (respectively) and/or the second value is 85, 90 or 95% absence or presence (respectively).

In some embodiments, either before the optional conversion to categorical data (operation 212) or after, the set of electrical signals is windowed or reduced to remove electrical signals associated with different electrodes that are highly correlated with each other. For example, the reception area of different electrodes may overlap so that they detect approximately the same electrical signals. These electrical signals may be removed from the set of electrical signals before attempting to identify the one or more association variables.

Additionally, or alternatively, in some embodiments at least some of the determined compound variables may be optionally excluded (operation 218) after determining the compound variables (216). For example, a given excluded compound variable may have a number of presence or absences in a pattern of occurrence of the compound variable (i.e., in the data determined from the one or more organisms using the electrodes) which is greater than a third value or less than a fourth value. This may exclude compound variables that have too few or too many presences or absences for there to be a statistically significant relationship with a pattern of occurrence of the neural activity. For these excluded compound variables, it may not be possible to determine whether or not there is a relationship with the neural activity. In an exemplary embodiment, the third value is 5, 10, or 15% presence or absence (respectively) and/or the fourth value is 85, 90 or 95% absence or presence (respectively).

As noted above, the compound variables may be determined (216). (Alternatively, the compound variables may be pre-determined, stored in a computer-readable memory, and accessed during process 200.) Moreover, as described further below, this determining or accessing may be iterated in operation 228 (FIG. 2B) at increasingly higher orders, which facilitates the identification of the one or more association variables using hierarchical feature extraction. For example, at first order, a given compound variable may correspond to a pattern of occurrence of a given electrical signal.

Then, at second order, a given compound variable may correspond to a pattern of occurrence of one electrical signal in the set of electrical signals and a pattern of occurrence of another electrical signal in the set of electrical signals. This process may be repeated at ever high order (i.e., with larger groups of electrical signals), until the resulting model complexity is sufficient to 'fit' the data or until diminishing returns occur (as described further below).

Note that the given compound variable for an order n may be determined by performing a mathematical operation and/or a logical operation on corresponding entries in the patterns of occurrence of n electrical signals. For example, at second order, a particular compound variable may be determined by performing the mathematical operation and/or the logical operation on corresponding entries in a pattern of occurrence of a first electrical signal and a pattern of occurrence of the second electrical signal (which is described further below with reference to FIG. 3B). Note that the mathematical operation may include multiplication. Moreover, the logical operation may include a Boolean operation, such as AND. However, a wide variety of coding approaches may be used in different embodiments for representing presence and/or absence information in the patterns of occurrence of electrical signals. Therefore, in some embodiments the logical operation may include AND, OR, NOT, XOR, and/or another Boolean operation.

More generally, for ternary encoded electrical signals (such as {0, 1 or 2} for the value of the electrical signal from a given electrode in a time interval proximate to the neural activity) the mathematical operation used to determine the given compound variable may be one of a set of mathematical operations. For example, the set of mathematical operations may be represented by 3×3 matrices, such as at least some of those provided in Wentian Li et al., "A Complete Enumeration and Classification of Two-Locus Disease Models," Human Heredity vol. 50, pp. 334-349 (2000). (Note that the set of mathematical operations may be selected based on those 3×3 matrices that are expected to provide the largest signal in the identification technique, such as the largest numbers of occurrences in the occurrence ranking.) Thus, the given compound variable may be determined by performing a mathematical operation specified by a given mathematical interaction on corresponding entries in a pattern of occurrence of the first electrical signal in the given pair of electrical signals and a pattern of occurrence of the second electrical signal in the given pair of electrical signals.

In some embodiments, one or more compound variables may be a weighted summation of one or more electrical signals. For example, for order n, n electrical signals may be multiplied by corresponding weights and summed to determine the given compound variable. Moreover, in some embodiments the resulting one or more compound variables may be converted into categorical data using one or more thresholds (thus, converting operation 212 may occur before and/or after the determining operation 216).

Figure 2B:
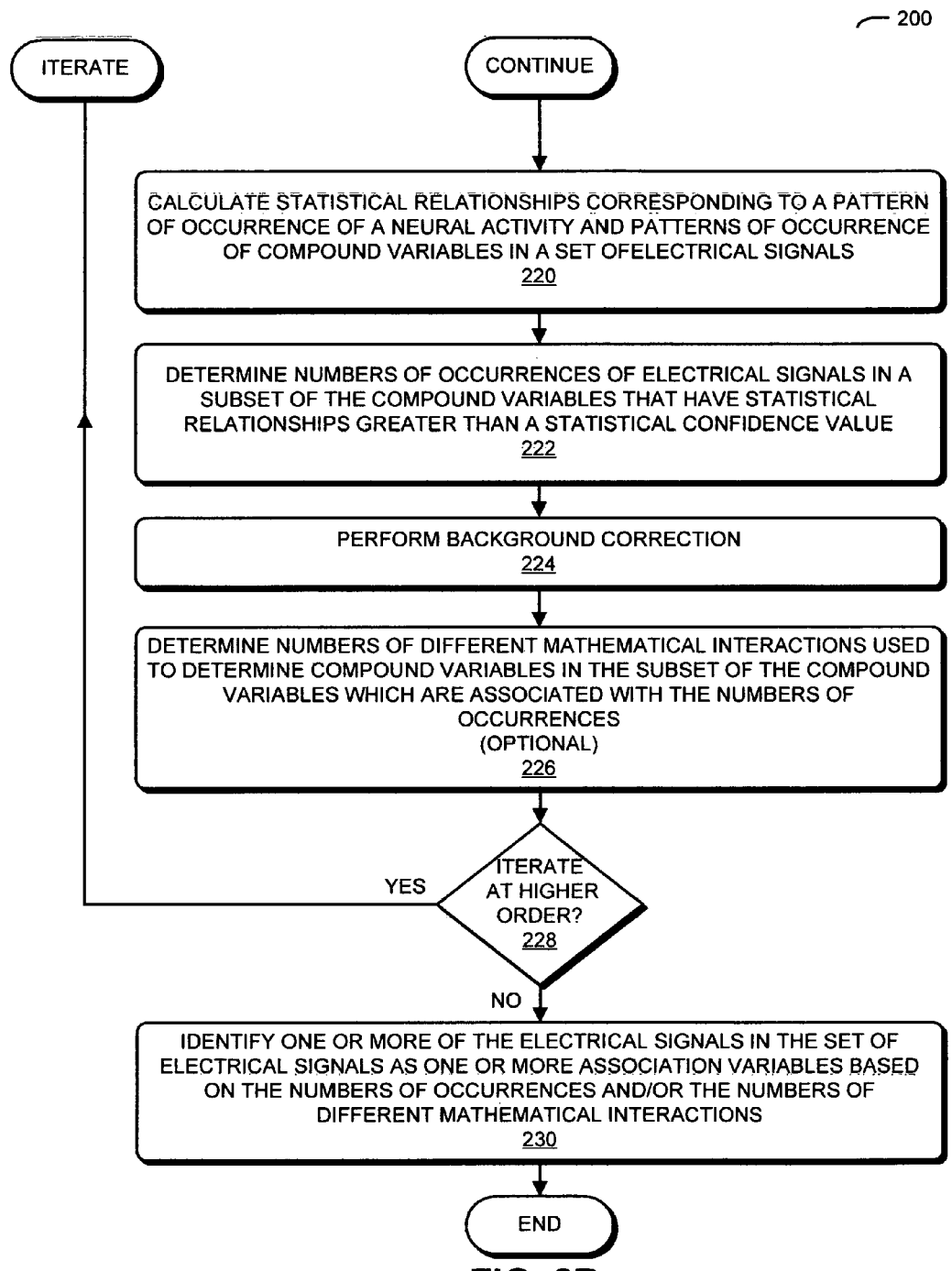
FIG. 2B is a flow chart illustrating a process for identifying one or more association variables that are associated with a neural activity in accordance with an embodiment of the present disclosure.

Continuing the discussion of process 200 in FIG. 2B, then statistical relationships corresponding to a pattern of occurrence of the neural activity and patterns of occurrence of compound variables in a set of electrical signals may be calculated (operation 220). In particular, a given statistical relationship may correspond to the pattern of occurrence of the neural activity for the one or more organisms and the pattern of occurrence of the given compound variable in the set of electrical signals. Note that the calculation may include contributions from presence and/or absence information in the pattern of occurrence of the given compound variable and/or in the patterns of occurrence of the neural activity.

As described further below, the statistical relationships may be determined using a supervised-learning analysis technique and/or a non-parametric analysis technique, which makes few assumptions about an existence of a probability distribution function (such as a normal distribution) corresponding to the electrical signals, or regarding independence of the electrical signals and/or the compound variables. In some embodiments, a given statistical relationship may be used to perform hypothesis testing to determine if the associated given compound variable and the neural activity are statistically independent (or dependent) based on a statistical confidence value (for example, based on a statistical significance value or criterion). In the process, the effective signal-to-noise ratio in an underdetermined problem (e.g., sparse sampling in a multi-dimensional variable space, such as when a number of entries in the pattern of occurrence of the neural activity (which correspond to one or more instances or repetitions of the neural activity performed by the one or more organisms) is significantly less than a number of electrical signals in the set of electrical signals) may be improved by restricting a number of local fitting neighborhoods (e.g., a number of relevant electrical signals and/or compound variables), thereby reducing the requirements associated with the Bonferonni correction.

Note that in some embodiments 'significantly less than' includes a multiplicative factor of 2, 5, 10, 100, 1000, $10^4$, $10^5$, $10^6$, $10^7$, or more. Thus, the number of entries for the pattern of occurrence of the neural activity may be at least 1000 times less than the number of electrical signals in the set of electrical signals. In an exemplary embodiment, the number of entries is between 100 and 1000 and the number of electrical signals in the set of electrical signals is between 1,000 and 15,000.

Next, numbers of occurrences of electrical signals that were used to determine the compound variables in a subset of the compound variables that have statistical relationships greater than a statistical confidence value may be determined (222). For example, an occurrence ranking based on the numbers of occurrences may be determined. (This is described further below with reference to FIGS. 4 and 5A.)

Moreover, a background correction may be performed (operation 224). For example, the additional statistical relationships may be calculated (as in operation 220) using a sequence of values (such as a random or a pseudorandom sequence having the same number of entries as the pattern of occurrence of the neural activity) instead of the pattern of occurrence of the neural activity. Then, another occurrence ranking for another subset of these additional statistical relationships that are significant may be determined (as in operation 222) and may be subtracted from the occurrence ranking. Note that significance of the other subset of the additional statistical relationships may be determined using another statistical confidence value, which may be different that the statistical confidence value.

Additionally, numbers of different mathematical interactions used to determine the compound variables in the subset of the compound variables for the electrical signals that are associated with the corresponding numbers of occurrences may be optionally determined (operation 226). For example, an interaction ranking of the electrical signals in the subset may be determined based on the numbers of different mathematical interactions associated with these electrical signals. (This is described further below with reference to FIG. 5B.)

As noted previously, operations 216-226 may be iterated (operation 228) using progressively higher-order compound variables to determine the statistical relationships and the rankings. In some embodiments, at least a portion of the occurrence ranking for the current order is used to determine the compound variables (216) (FIG. 2A) at the next higher order. As described further below, these iterations may be continued until a model that describes the relationship between the patterns of occurrence of the compound variables in the set of electrical signals and the pattern of occurrence of the neural activity is obtained or diminishing returns occur (such as an increase in an error associated with predictions of the model based on training data and test data).

Next, one or more of the electrical signals in the set of electrical signals may be identified (operation 230) as the one or more association variables based on the numbers of occurrences (e.g., the occurrence ranking) and/or the numbers of different mathematical interactions (e.g., the interaction ranking). As described further below with reference to FIG. 5A, the one or more association variables may be identified in occurrence rankings that are above a noise floor in the statistically significant compound variables. For example, at least a subset of such occurrence rankings may be approximately stable, and the electrical signals in such subsets may be the one or more association variables. As is also described further below, note that the one or more association variables may have a relationship or an anti-relationship with the occurrence of the neural activity.

In some embodiments, process 200 includes additional or fewer operations. Moreover, the order of the operations may be changed and/or two or more operations may be combined into a single operation. For example, in some embodiments compound variables may be determined (216) (FIG. 2A) using electrical signals associated with time intervals (which may be the same as each other, may be different than each other, and/or may be offset from each other) that precede and/or follow the neural activity (such as moving a finger). In some embodiments, the time intervals include: 1 ms, 2 ms, 5, ms, 10 ms, 20, ms, 50 ms, 100 ms, 125 ms, 200 ms, etc. In an exemplary embodiment, at second order, a particular compound variable corresponds to a pattern of occurrence of a first electrical signal in a first time interval proximate to the neural activity and a pattern of occurrence of a second electrical signal in a second time interval proximate to the neural activity.

In some embodiments, at least some of the operations in process 200 are repeated to identify subgroups or subpopulations in the one or more organisms. For example, one or more subgroups may be determined based on the one or more identified association variables for different portions or subsets of the one or more organisms.

Figure 3A:
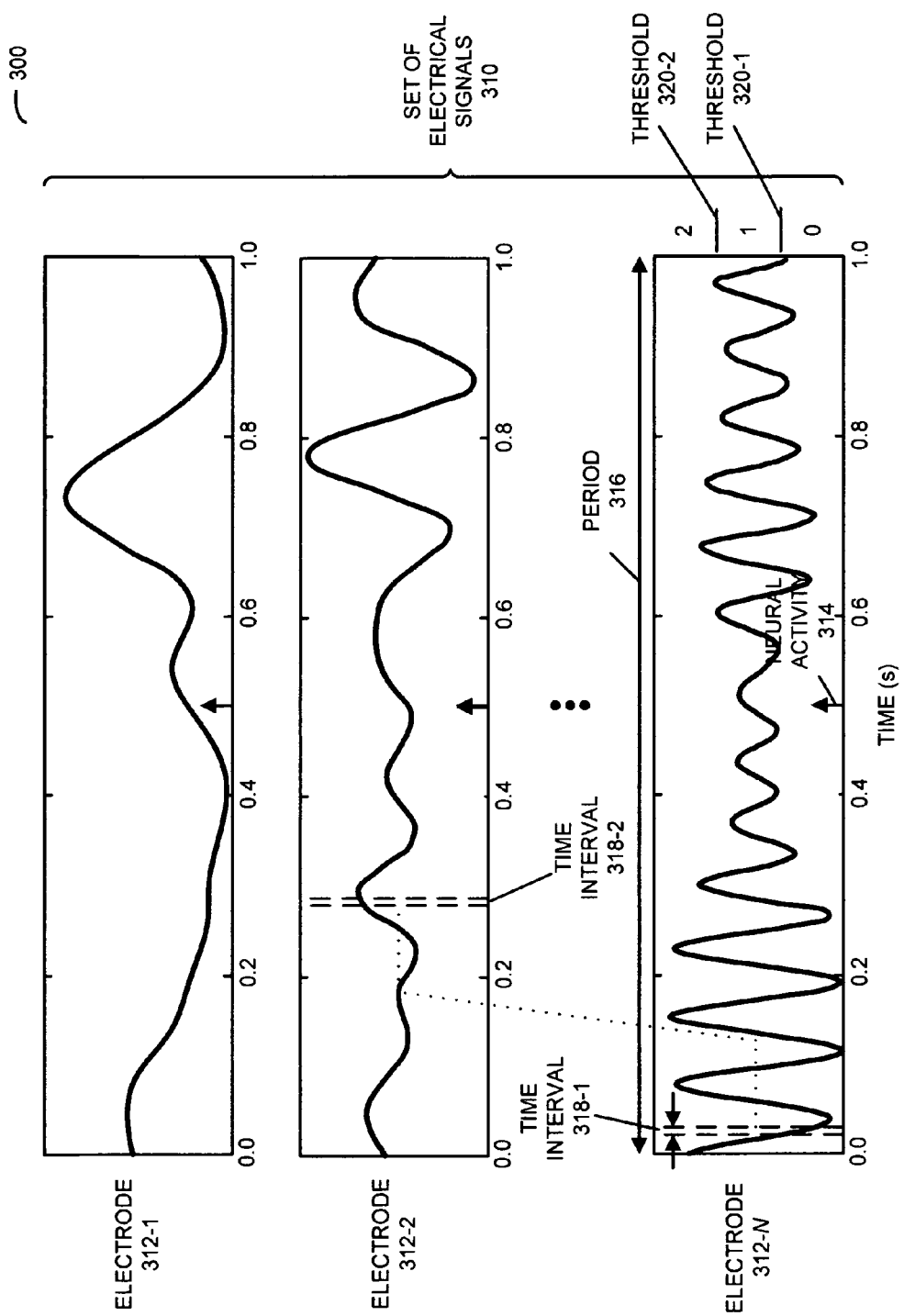
FIG. 3A is a drawing illustrating identifying one or more association variables that are associated with a neural activity in accordance with an embodiment of the present disclosure.

We now describe examples of operations in process 200. FIG. 3A presents a drawing 300 illustrating identifying one or more association variables that are associated with a neural activity. Set of electrical signals 310 may include multiple electrical signals (the columns) associated with electrodes 312 that are placed on or near an organism. For example, electrodes 312 may be placed: deep in the brain, on the surface of brain, and/or on the surface of the scalp. These electrical signals may be measured proximate (before, during and/or after) to a neural activity 314. Moreover, neural activity 314 may be repeated one or more times, with each instance or repetition having period 316.

The electrical signals may be sampled. For example, the samples may represent the average values in time intervals, such as time intervals 318. In an exemplary embodiment, the samples have ternary values as determined based on thresholds 320. For example, if an electrical signal is less than threshold 320-1 during a time interval, the resulting sample may be a '0'; if the electrical signal is less than threshold 320-2 and greater than threshold 320-1 during the time interval, the resulting sample may be a '1'; and if the electrical signal is greater than threshold 320-2 during the time interval, the resulting sample may be a '2.'

The resulting dataset may include multiple dimensions or vectors, a given one of which includes the sampled values during a given time interval in the period of a given electrical signal measured using a given electrode. Furthermore, the entries in these vectors may represent the sampled values during the given time interval in multiple instances or repetitions of the neural activity. Depending on the number of repetitions performed by a given organism, the entries in the vectors may be for a single organism is multiple organisms (i.e., the dataset may aggregate the data from two or more organisms).

Note that the entries in the given vector specify a pattern of occurrence of the given electrical signal. Similarly, the presence or absence of the neural activity during the time intervals specifies the pattern of occurrence of the neural activity. Moreover, a subset of the data for the pattern of occurrence of the neural activity may be used so that the pattern of occurrence of the neural activity may include 50% presence and 50% absence (such as 50% 1s and 50% 0s).

This is shown in FIG. 3B, which presents a drawing 350 illustrating identifying one or more association variables that are associated with a neural activity. In this drawing, set of electrical signals 360 include vectors with ternary-valued samples during the time intervals and the multiple entries in set of electrical signals 360 are associated with multiple repetitions of instances 362 of the neural activity in one or more organisms. Using pairs of vectors and a given mathematical interaction (which may be represented by a 3×3 matrix), a compound variable 364 having binary values is determined. For example, at second order, entries in two time-interval vectors in set of electrical signals 360 may be combined according to a particular mathematical operation, such as the M21 penetrance table in Wentian Li et al. In this case, if an entry in a first electrical signal is a '0' and an entry in a second electrical signal is a '1', this specifies row 0, column 1 in the M21 penetrance table, which results in a row entry of a '0' in compound variable 364. In general, the resulting entries in compound variable 364 may vary across or over the multiple instances or repetitions. This variation defines the pattern of occurrence of compound variable 364.

Then, the statistical relationship (such as a statistical association) with neural vector 366 (which includes sampled values during the period, including '1s' during the neural activity and '0s' when the neural activity is not occurring) is calculated. In particular, the pattern of occurrence of compound variable 364 and the pattern of occurrence of neural vector 366 may be used on an entry-by-entry or row-by-row basis to calculate the statistical association. For example, the statistical association may be determined by comparing entries in compound variable 364 and neural vector 366 using a statistical analysis technique.

This process may be repeated for multiple combinations of the electrical signals in set of electrical signals 360 (i.e., multiple compound variables may be determined based on the same or different mathematical operations in the set of mathematical operations) to generate a set of statistical relationships with neural vector 366 for a given order in the analysis. For example, all pairwise permutations and combinations of vectors may be used to determine compound variables. As described further below with reference to FIGS. 4-6, the aggregate properties of the statistically significant subset of compound vectors (such as the occurrence ranking and the interaction ranking) may be used to identify the association variable(s).

In an exemplary embodiment, period 316 (FIG. 3A) is between 1-10 s, there are 100-5000 entries in the vectors, time intervals 318 (FIG. 3A) are between 1-16 ms, there are 1-256 electrodes, and set of electrical signals 360 is ternary encoded. For example, there may be at least five or seven electrodes on the: forehead, occiput, left side of the head, the right side of the head, and on top of the head (thereby collecting electrical signals associated with the frontal lobe, the occipital lobe, the left temporal lobe, the left parietal lobe, the right temporal lobe, and/or the right parietal lobe. Furthermore, the data may be analyzed using up to the 100 mathematical interactions specified by specified in Wentian Li et al., such as penetrance tables: M1, M3, M7, M10, M11, M13, M14, M17, M21, M26, M27, M30, M41, M42, M45, M58, M69, M78, M85, M86, M97, M99, M101, M106, M113, M114, M170, and M186. These mathematical interactions allow compound variables to be determined at second order, i.e., using pairs of electrical signals. For example, with 76 electrodes, 100 time intervals in the period, and 100 mathematical interactions, a total of $5.776 \times 10^9$ compound variables may be determined. These vectors may each have 100-5000 entries.

Figure 4:
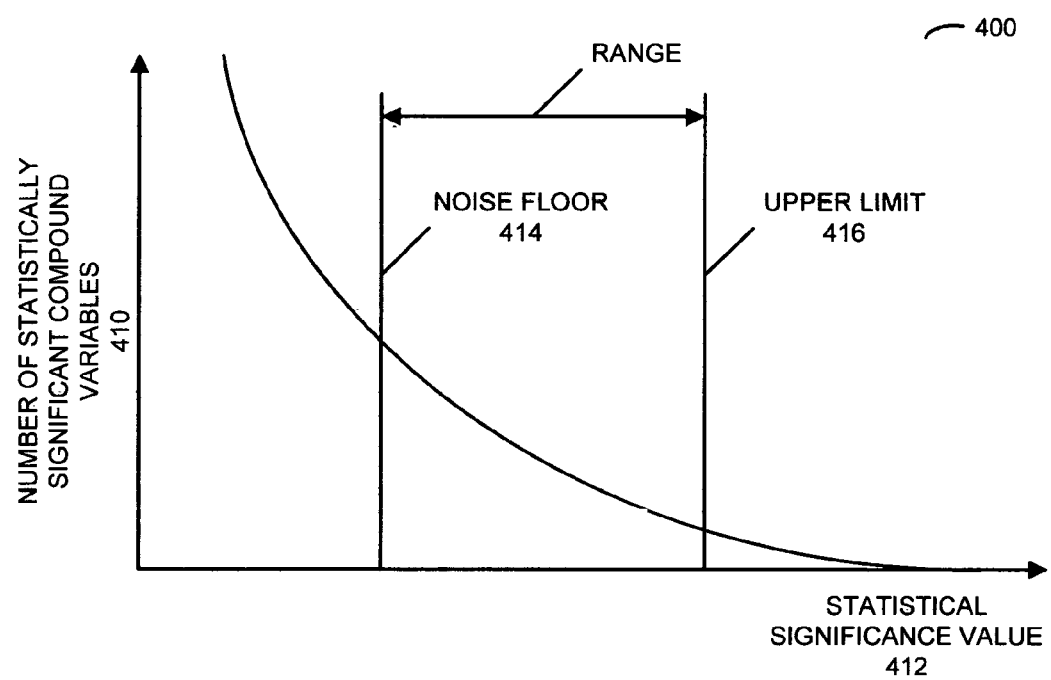
FIG. 4 is a graph of a number of statistically significant compound vectors as a function of statistical significance value in accordance with an embodiment of the present disclosure.

After calculating the set of statistical relationships, they may be compared to statistical confidence values (such as a statistical significance value or criterion) to identify a noise floor in the set of statistical relationships. This is shown in FIG. 4, which presents a graph 400 of a number of statistically significant compound vectors 410 (i.e., compound vectors having statistical relationships with the neural activity that exceed a statistical significance value) as a function of statistical significance value 412. As the statistical significance value 412 is increased, the number of statistically significant compound vectors 410 decreases. If the signal-to-noise ratio in the set of electrical signals 360 (FIG. 3B) and neural vector 366 (FIG. 3B) is sufficiently large (for a given size of or number of instances or repetitions of the neural activity) then at least a portion of occurrence rankings of the numbers of occurrences of electrical signals in the statistically significant compound vectors 410 between a minimum value of the statistical significance value 412 and an upper value 416 of the statistical significance value 412 is substantially or approximately stable. (One metric for whether or not the signal-to-noise ratio is sufficiently large may be that the expectation value for the number of statistically significant compound variables for a given statistical significance value is less than the actual number of statistically significant compound vectors at the given statistical significance value.) This minimum value may be noise floor 414. Note the upper value 416 occurs because, eventually, as the statistical significance value 412 is increased, the number of statistically significant compound vectors 410 decreases to the point where the remaining statistically significant compound vectors 410, and thus the corresponding occurrence rankings, are dominated by statistical outliers. Consequently, for a large enough statistical significance value 412, the occurrence ranking may no longer be substantially or approximately stable.

Figure 5A:
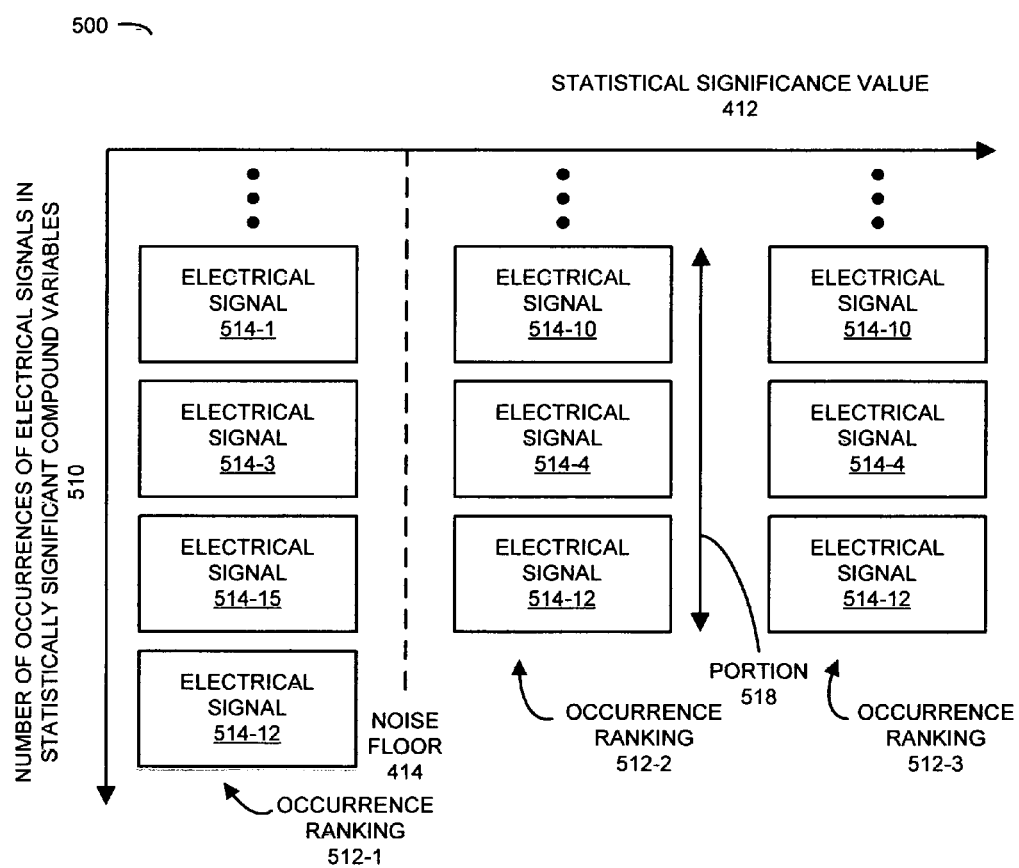
FIG. 5A is a drawing of an occurrence ranking of numbers of occurrences of electrical signals in statistically significant relationships as a function of statistical significance value in accordance with an embodiment of the present disclosure.

FIG. 5A presents a drawing 500 of an occurrence ranking of numbers of occurrences of electrical signals in statistically significant compound variables 510 as a function of statistical significance value 412. As statistical significance value 412 increases, at least a portion 518 of occurrence rankings, such as occurrence rankings 512-2 and 512-3, above noise floor 414 is substantially or approximately stable. (In contrast, occurrence ranking 512-1 may not be stable, i.e., when the statistical significance value 412 increases, occurrence ranking 512-1 may change.) For example, a given occurrence ranking, such as occurrence ranking 512-2, may be considered to be substantially or approximately stable if 50%, 70%, 75%, 80%, 85%, 90%, 95% or 100% of the top-N electrical signals (such as the top-20) in the given occurrence ranking are unchanged when the statistical significance value 412 is increased.

Note that portion 518 may include one or more electrical signals 514. Moreover, at least portion 518 in occurrence rankings 512-2 and 512-2 may indicate or specify a pareto. Furthermore, the one or more association variables may be identified in portion 518 or in occurrence rankings 512-2 and 512-3 that are substantially or approximately stable.

Figure 5B:
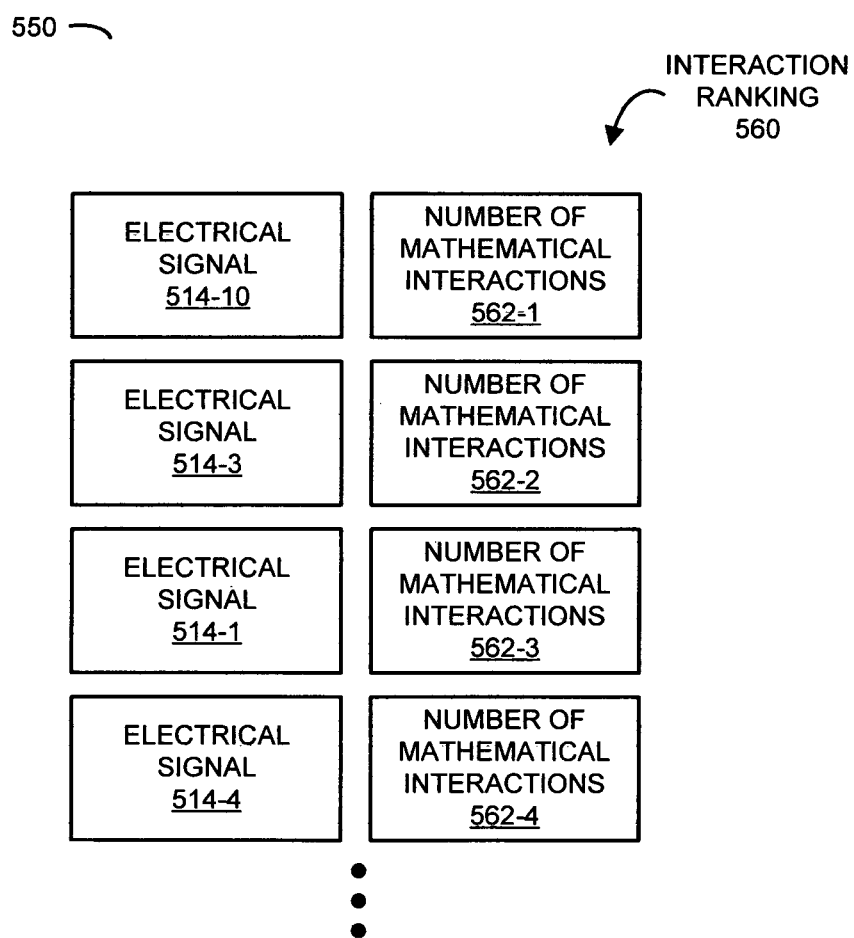
FIG. 5B is a drawing of an interaction ranking of numbers of different mathematical interactions used to determined compound variables in a statistically significant subset of the compound variables that are associated with the corresponding numbers of occurrences in accordance with an embodiment of the present disclosure.

Once a substantially or approximately stable occurrence ranking is determined, it can be used to determine an interaction ranking. This is shown in FIG. 5B, which presents a drawing 550 of an interaction ranking 560 of numbers of different mathematical interactions used to determined compound variables in a statistically significant subset of the compound variables that are associated with the corresponding numbers of occurrences. In particular, interaction ranking 560 may provide a pareto of electrical signals 514 based on a number of different mathematical interactions 562 with which they are used to determine compound variables in the statistically significant subset of the compound variables. In this example, electrical signal 514-10 is at the top of interaction ranking 560. Electrical signal 514-10 may occur 500 times in the tens of thousands of statistically significant compound variables, and 20 different mathematical interactions may have been used, in conjunction with electrical signal 514-10, to determine these 500 compound variables. Similarly, electrical signal 514-3 is second in interaction ranking 560. Electrical signal 514-3 may occur 100 times in the tens of thousands of statistically significant compound variables, and 14 different mathematical interactions may have been used, in conjunction with electrical signal 514-3, to determine these 100 compound variables.

Note that the assumption that underlies occurrence rankings 512 (FIG. 5A) and interaction ranking 560 is that the electrical signals interact with each other according to a graph with nodes and branches. While the underlying interactions are assumed to be biological in nature (e.g., they may correspond to the topology of the graph), in the present analysis the interactions are studied and identified based on mathematical interactions (which may or may not reflect the underlying biological interactions). In this graph, nodes that are more important are those that have more branches. Thus, by considering the number of occurrences of a given node in the subset, the relative importance of the given node relative to other nodes in the graph can be assessed using an occurrence ranking.

Similarly, the mathematical interactions provide very selective filtering as the electrical signals are combined to determine compound variables. As the order n is increased, it is increasingly difficult to find a pattern of occurrence of a given electrical signal for a given mathematical interaction that, in conjunction with a compound variable of order n−1, improves the statistical association with the pattern of occurrence of the neural activity. (In fact, using the given mathematical interaction the pattern of occurrence of the given electrical signal typically results in a weaker statistical association.) In general, if a first mathematical interaction for a pair of electrical signals results in a statistically significant association, a different mathematical interaction is needed to determine a statistically significant association between a third electrical signal and either of the electrical signals in the pair of electrical signals. Thus, assuming that the graph includes sequences of multiple interacting nodes (i.e., electrical signals), these can be identified by looking for electrical signals that are associated with multiple different mathematical interactions in an interaction ranking.

We now further describe embodiments of the statistical analysis. This statistical analysis may include classification and/or regression (such as determining a model of the one or more neural activities, which includes one or more electrical signals and/or one or more compound variables, along with corresponding weights).

A wide variety of computational techniques may be used to determine the one or more statistical relationships, including: one or more parametric analysis techniques, one or more non-parametric analysis techniques, one or more supervised learning techniques and/or one or more unsupervised learning techniques. In some embodiments, one or more non-parametric analysis techniques may be used. As noted previously, non-parametric analysis techniques make few assumptions about an existence of a probability distribution function, such as a normal distribution, corresponding to the one or more organisms from which samples or associated data are obtained, or regarding independence of the electrical signals and/or the compound variables. In general, non-parametric analysis techniques may use rank or naturally occurring frequency information in the data to draw conclusions about the differences between different populations or subsets of the given population.

Note that the one or more non-parametric analysis techniques may perform hypothesis testing, e.g., to test a statistical significance of a hypothesis. In particular, the one or more non-parametric analysis techniques may determine if the one or more neural activities and/or the one or more compound variables are statistically independent (or dependent) based on a statistical significance value or criterion. As noted previously, one or more compound variables having a statistically significant relationship with the neural activity (and, in particular, the pattern of occurrence of the neural activity) may be used to identify the one or more association variables.

In exemplary embodiments, the non-parametric analysis technique may include: a chi-square analysis technique, a log-likelihood ratio analysis technique (also referred to as G-test), and/or a Fisher's exact probability analysis technique. In addition to their other advantages, these techniques may be well suited to analyzing an underdetermined problem, i.e., sparse sampling in a multi-dimensional variable space, in which there may be multiple electrical signals and/or compound variables and a smaller number of entries in these variables and in the neural-activity information (i.e., the pattern of occurrence of the neural activity).

In some embodiments, the chi-square analysis technique, the log-likelihood ratio analysis technique, and/or the Fisher's exact probability analysis technique may be determined using a cross-tabulation or contingency tables (which are sometimes referred to as bivariate tables). Note that the Fisher's exact probability analysis technique computes the sum of conditional probabilities of obtaining the observed frequencies in a given contingency table and the conditional probabilities of obtaining exactly the same observed frequencies for any configuration that is more extreme, i.e., having a smaller conditional probability. Moreover, the chi-square ($\chi^2$) may be determined using $$\chi^2 = \sum_i \frac{(O_i - E_i)^2}{E_i},$$

and the log-likelihood ratio (LLR) using $$LLR = \sum_i O_i \ln\left(\frac{O_i}{E_i}\right),$$

where the summation is over the entries in the given contingency table, $O_i$ is the i-th observed frequency value, and $E_i$ is the i-th expected frequency value. The following example illustrates an exemplary embodiment of determining a statistical relationship using the log-likelihood ratio for binary categorical data.

Consider the example contingency table in Table 1. The first column contains the number of entries in the pattern of occurrence where a compound variable is present and the neural activity is present (which is henceforth denoted by $X_{11}$) in the data (such as the set of electrical signals) plus the number of entries in the pattern or occurrence where the compound variable is absent and the neural activity is absent in the data (which is henceforth denoted by $X_{00}$). $X_{11}$ is sometimes referred to as a true-true and $X_{00}$ is sometimes referred to as a false-false. $X_{11}$ and $X_{00}$ are henceforth referred to as co-occurrences.

The second column in Table 1 contains the number of entries in the pattern of occurrence where the compound variable is present and the neural activity is absent (henceforth denoted by $X_{10}$) in the data plus the number of entries in the pattern of occurrence where the compound variable is absent and the neural activity is present (henceforth denoted by $X_{01}$) in the data. $X_{10}$ is sometimes referred to as a true-false and $X_{01}$ is sometimes referred to as a false-true. $X_{10}$ and $X_{01}$ are henceforth referred to as cross occurrences.

TABLE 1

| Number of Co-Occurrences ($X_{11} + X_{00}$) | Number of Cross Occurrences ($X_{10} + X_{01}$) |
| --- | --- |
| 46 | 11 |

If the compound variable and the neural activity are completely independent, the expected frequency values for each column, $E_1$ and $E_2$, would equal 28.5, one half of the sum of the number of co-occurrences and cross occurrences, i.e., the total number of observations (data points or observations) in Table 1. Therefore, for Table 1, $LLR=2\cdot46 \ln(46/28.5)+2\cdot11 \ln(11/28.5)=44.04-20.94=23.10.$ A one-sided minimal statistical significance confidence value or criterion of 5% ($\alpha=0.05$) or a statistical confidence threshold based on the number of degrees of freedom (the size of the contingency table, which in this example is one) corresponds to an LLR of 3.841. (Note that if the electrical signals have more than two categories, the contingency table may have a larger number of degrees of freedom.) Because the LLR for Table 1 is greater than 3.841, it is statistically significant. Therefore, from a statistical perspective, the null hypothesis is rejected and the patterns of occurrence of the compound variable and the neural activity in this example are dependent.

Note that it is possible for statistically significant LLR values to occur even when $X_{11}$ is zero. In some embodiments, compound variables that have $X_{11}$ equal to zero when compared with the pattern of occurrence of the neural activity are excluded prior to determining the rankings and identifying the one or more association variables. Additionally, note that the LRR value is the same when there is a relationship (when the number of co-occurrences is greater than the number of cross occurrences) or an anti-relationship (when the number of co-occurrences is less than the number of cross occurrences) between the pattern of occurrence of the compound variable and the pattern of occurrence of the neural activity. Consequently, in embodiments where association variables corresponding to relationships are desired, statistical relationships where the number of co-occurrences is less than the number of cross occurrences may be excluded. Similarly, in embodiments where association variables corresponding to anti-relationships are desired, statistical relationships where the number of co-occurrences is greater than the number of cross occurrences may be excluded. Furthermore, in some embodiments, instead of using an occurrence ranking corresponding to the sequence of values to perform the background correction, an occurrence ranking of the number of occurrences of electrical signals in statistical relationships corresponding to no relationship (i.e., an LLR of infinity, or when the number of co-occurrences equals the number of cross occurrences) may be used.

In the preceding example, the calculation of the statistical relationship for the neural activity and the compound variable uses presence and absence information in the patterns of occurrence of the compound variable and the neural activity. In some embodiments, one or more of the statistical relationships may be determined using presence information, i.e., the presence only (or absence only) of one or more compound variables, without using absence information (or without using presence information). In alternate embodiments, a wide variety of analysis techniques may be used to calculate the one or more statistical relationships.

In parametric analysis, a Pearson's product-moment correlation coefficient r may be useful in summarizing a statistical relationship. For some contingency tables, Cramer's phi $\phi$, the square root of $\chi^2$ or the LLR divided by the number of observations N, may have a similar interpretation to r (although, it is known that Cramer's phi $\phi$ may underestimate r). In the example illustrated in Table 1, $$\varphi = \sqrt{\frac{LLR}{N}} = \sqrt{\frac{23.1}{57}} = 0.64.$$

The chi-square analysis technique and the log-likelihood ratio analysis technique may have a maximal sensitivity for contingency tables based on the pattern of occurrence of the neural activity having 50% presence entries and 50% absence entries. In some embodiments, one or more contingency tables may be generated to achieve approximately 50% presence entries and 50% absence entries for patterns of occurrence of one or more compound variables by using a subset of the data. In an exemplary embodiment, one or more contingency tables may be generated by randomly or pseudo-randomly selecting (for example, using a pseudo-random number generator or technique) a subset of the data, such that the one or more contingency tables may have approximately 50% presence entries and 50% absence entries distributed over $X_{00}$, $X_{11}$, $X_{10}$, and $X_{01}$. For infrequently occurring events, the electrical signals and/or compound variables may have more absence entries than presence entries (such as an absolute value of a positive or negative electrical signal exceeding a threshold). As a consequence, different sampling ratios may be used for presence and absence entries in the data.

In some embodiments, boosting may be used when generating one or more contingency tables. A subset of the data may be selected randomly or pseudo-randomly in order to determine one or more contingency tables. A given contingency table may be generated L times using approximate random sampling. Statistical relationships for at least M of these L contingency tables may be used (including combining and/or averaging) to determine whether or not the neural activity and the corresponding compound variable are independent in the data. In an exemplary embodiment, L may be 5, 10, 25, 50, 100, 500 or more, and M may be 50% (rounded to the nearest integer), 60%, 66%, 70%, 75%, 80% or more of L.

In some embodiments, there may be too few presence entries or too many presence entries in one or more patterns of occurrence of one or more electrical signals or compound variables in the data to reliably determine statistically significant independence (or dependence) based on the neural-activity information. As a consequence, one or more of these electrical signals or one or more of these compound variables may be excluded when determining one or more statistical relationships. In an exemplary embodiment, one or more electrical signals or one or more compound variables having patterns of occurrence with less than 15% presence entries or more than 85% presence entries in the data may be excluded.

Overfitting or developing a model that is too complex is a risk in a statistical learning problem. In some embodiments, the model complexity may correspond to a number of compound variables that have statistically significant dependence on the neural-activity information. Moreover, in some embodiments the model complexity may, at least in part, correspond to a number of electrical signals included when determining a given compound variable, i.e., the order n.

In some embodiments, this risk may be addressed using a fraction or percentage of the data (such as the patterns of occurrence) for training, i.e., to develop the model, and a remainder for testing the resulting model. Typically training error decreases as the model complexity increases (the model better fits or predicts a training set of data), and a testing error exhibits a minimum. Additional model complexity beyond this minimum usually does not generalize well (the model offers a poorer fit or prediction for a test set of data). Therefore, beyond the minimum point the training set of data may be overfit. In an exemplary embodiment, the percentage of the data used for training may be 70%, 75%, 80%, 85% or 90%.

An additional metric of the model complexity may be determined. This metric may be used in conjunction with or independently of the training set of data and the test set of data. The additional metric is described below. In some problems and/or embodiments, calculating one or more statistical relationships for one or more electrical signals (or, said differently, for one or more compound variables of order 1) may not be sufficient to determine statistically significant independence (or dependence) with respect to the neural-activity information. For example, in multi-dimensional problems, where two or more electrical signals are necessary and sufficient to give rise to a neural activity, a value of the Fisher's exact probability, $\chi^2$, and/or LLR for a compound variable of order 1 may be reduced since there is a penalty for the presence of the cross occurrences, $X_{10}$ and $X_{01}$.

More generally, the value of the Fisher's exact probability, $\chi^2$, and/or LLR may be reduced if the order n of one or more compound variables is less than an intrinsic order of the multi-dimensional problem. In the case of $X_{10}$, a neural activity may or may not occur unless a certain number of electrical signals or a set of electrical signals (which may be inter-operative) are present. And in the case of $X_{01}$, more than one set of electrical signals may be present, i.e., one or more electrical signals in another set of electrical signals may lead to the neural activity. (Moreover, for environmental factors, there may be one or more thresholds, which may be a function of time.)

To assess whether or not the model has sufficient complexity, i.e., whether or not one or more compound variables have been determined to sufficient order n, a ratio R may be determined. For contingency Table 1, R is defined as $X_{11}$ divided by the total number of occurrences of the compound variable of order n in the data, i.e., $$R = \frac{X_{11}}{(X_{11} + X_{10})}.$$

An increasing value of R, and/or Cramer's phi $\phi$, as statistical analysis is performed to higher order (i.e., n+1) may be metrics of goodness, i.e., it may indicate that the higher order does a better job determining statistically significant independence or dependence between one or more compound variables and the neural-activity information. In some embodiments, contingency tables for one or more compound variables may be generated for progressively higher orders (e.g., by iterating at least some of the operations in process 200 in FIGS. 2A and 2B). Once the ratio R is close to or equal to one, i.e., $X_{10}$ is close to or equal to zero, further increases in the order n of one or more compound variables may not be needed (the model has sufficient complexity). Note that in some embodiments, statistical entropy may be used to determine if further increases in the order n of one or more compound variables are needed.

One or more variables and/or compound variables having statistically significant statistical relationships with the neural-activity information may be identified as one or more association variables. For a given compound variable of order n having a significant statistical relationship with the neural-activity information, the n constituent electrical signals may be identified as n association variables and/or as a set of association variables. In some embodiments, one or more statistically significant compound variables of order n having the ratio R approximately equal to 1 may be identified as one or more association variables.

In some embodiments, one or more compound variables of order n and/or one or more constituent electrical signals in the one or more compound variables of order n may be ranked based on the corresponding calculated statistical relationships that are statistically significant. In some embodiments, an occurrence ranking of a given constituent electrical signal is based on a number of occurrences of the given constituent electrical signal in one or more compound variables of order n having statistical relationships that are statistically significant. As noted previously, occurrence rankings may be performed as the statistical significance confidence value or criterion ($\alpha$) is progressively increased, which can be used to determine the noise floor in the statistical relationships (as described previously in the discussion of FIG. 4, and as described further below). Additionally, once a suitable statistical significance confidence value or criterion is found (based on substantial or approximate stability of the occurrence rankings), an interaction ranking may be determined based on the numbers of different mathematical interactions used to determine the compound variables in the subset of the compound variables for the electrical signals that are associated with the corresponding numbers of occurrences.

In exemplary embodiments, $\alpha$ may be 0.05 or lower. For a given occurrence ranking, a pareto corresponding to at least a portion of the given occurrence ranking may be defined. This pareto may correspond to electrical signals or compound variables having a statistical relationship or a number of occurrences in the statistically significant compound variables exceeding a threshold. In some embodiments, a top-10, 20, 50 or 100 electrical signals or compound variables may be used, or a majority of the top-10, 20, 50 or 100 electrical signals or compound variables may be used. For compound variables of order n, approximate stability of the pareto as the statistical significance value or criterion is increased may be used to identify the noise floor. 'Approximate stability' may include an approximately unchanged order of the ranking or a presence of approximately the same electrical signals and/or compound variables (for example, more than 70 or 80%) in the portion of the occurrence ranking. In exemplary embodiments, the noise floor may correspond to an $\alpha$ of 0.01 or lower, an $\alpha$ of 0.001 or lower, or an $\alpha$ of 0.0001 or lower.

Additionally, once a suitable statistical significance confidence value or criterion is found (based on substantial or approximate stability of the occurrence rankings), an interaction ranking may be determined based on the numbers of different mathematical interactions used to determine the compound variables in the subset of the compound variables for the electrical signals that are associated with the corresponding numbers of occurrences. One or more electrical signals and/or one or more compound variables in paretos corresponding to one or more statistical significance values or criteria that exceed the noise floor and which may be associated with the largest numbers of different mathematical interactions may be identified as association variables.

In some embodiments, the analysis is repeated using a random or pseudo-random sequence of values instead of the neural-activity information. This sequence of values may have the same length (or number of entries) as the pattern of occurrence of the neural activity. Moreover, the resulting occurrence ranking, which may be determined using the same or a different statistical significance value or criterion as the occurrence ranking described above, may be subtracted from the occurrence ranking described above before the one or more association variables are identified.

In some embodiments, one or more electrical signals and/or one or more compound variables in paretos corresponding to one or more statistical significance values or criteria that exceed the noise floor may be used as a seed set in additional statistical analysis. The additional statistical analysis may determine statistical relationships for compound variables of a higher order. In some embodiments, the additional analysis may utilize an analysis technique, such as SVM or CART.

Alternatively, the additional analysis technique may be used as the initial or first stage, to refine the model (including adding or removing one or more electrical signals and/or one or more compound variables), and/or to identify one or more association variables.

Note that the additional analysis technique may include classification and/or regression (such as determining a model of the neural-activity information including one or more electrical signals and/or one or more compound variables, along with corresponding weights). As with the statistical analysis technique described previously, a wide variety of techniques may be used in the additional analysis technique. Two such techniques, SVM and CART, are described further below.

Embodiments of SVM are instances of supervised learning techniques that may be applied to classification and regression problems. For binary classification, a set of binary labeled data points (training data or examples) is provided. SVMs may be used to determine an optimal separation boundary, defined by the electrical signals and/or compound variables, between two classes of data points. A separation boundary is optimal if using it as a decision rule to classify future data points minimizes an expected classification error. For linearly separable data sets (e.g., a class of absences, which may be indicated by −1, and a class of presences, which may be indicated by +1, that may be separated from each other by a line in 2 dimensions, or a so-called hyperplane in higher dimensions), SVMs may be used to determine a maximal margin hyperplane. For the maximal margin hyperplane, a linear decision boundary may be positioned such that it separates both classes and such that the distance to the closest point from each class is maximized. For non-linearly separable data sets, some training data points may be allowed on the opposite or 'wrong' side of the hyperplane, e.g., a classification error on the training data set may be allowed and may be minimized, while the margin, measured between points on the 'correct' side of the hyperplane, may be maximized.

If a linear decision boundary is not sufficiently complicated to model the separation between classes accurately, the corresponding linear model may be transformed into a non-linear model by non-linearly transforming the electrical signals and/or compound variables into a possibly higher dimensional Euclidean space. A linear decision boundary constructed in such a higher dimensional Euclidean space may correspond to a non-linear decision boundary in the original space of electrical signals and/or compound variables. This approach is referred to as kernel SVM.

Depending on how the margin and training error are measured, and how a trade-off between maximizing the margin and minimizing the training error is established, different types of SVMs may be obtained. In some embodiments, SVM may include standard 1-norm SVM (measuring the margin using Euclidean distance, i.e., a $L_2$-norm, and the training error using a $L_1$-norm), standard 2-norm SVM (measuring the margin using Euclidean distance, i.e., the $L_2$-norm, and the training error using the $L_1$-norm), and/or LP-SVM (measuring the margin using the $L_1$-norm and the training error using the $L_1$-norm). Each of these 3 types of SVM may be a C-type or η-type SVM. These two varieties correspond to different ways of trading-off maximizing the margin against minimizing the training error. The 1-norm SVM, standard 2-norm SVM, and/or LP-SVM may be a C+/C− or η+/η− type, where errors on positive (+1) labeled training data are weighted differently than errors on negative (−1) labeled training data.

The principle for binary classification described above may be extended to regression, for example, by copying the regression data twice, shifting both copies in opposite directions (over a distance epsilon) with respect to the continuous output dimension or variable and establishing a regression surface as a decision boundary between the two shifted copies that may be regarded as two classes for binary classification. As a consequence, in some embodiments, regression versions of SVMs corresponding to previously described SVMs may be used.

The decision boundary determined using one or more SVMs may be used to discriminate between presence and absence of the neural activity in the neural-activity information associated with the one or more organisms. For binary classification, measures of goodness for the resulting model include a prediction accuracy that is better than predicting 50% of the positive data (e.g., occurrences, which may be indicated by a +1) as positive (i.e., true positive predictions) and better than predicting 50% of the negative data (i.e., absences, which may be indicated by a −1) as negative (i.e., true negative predictions). Doing better than 50/50 corresponds to doing better than random.

CART is a non-parametric multivariate analysis technique. It involves the determination of a binary decision tree using the training set of data. Predictions based on the resulting tree may be compared to the test set of data (cross validation). A decision tree provides a hierarchical representation of the feature space in which explanatory variables are allocated to classes (such as presence or absence of the neural activity in the neural-activity information) according to the result obtained by following decisions made at a sequence of nodes at which branches of the tree diverge. Branches or divisions of the tree may be chosen to provide the greatest reduction in the statistical entropy of the variables (for a classification tree based on categorical data), such as a small or zero standard deviation, or the greatest reduction in the deviation between the electrical signals (and/or compound variables) and the neural activity being fit (for a regression tree based on quantitative data). A tree stops growing when no significant additional reduction can be obtained by division. A node that is not further sub-divided is a terminal node. It is associated with a class. A desirable decision tree is one having a relatively small number of branches, a relatively small number of intermediate nodes from which these branches diverge, terminal nodes with a non-zero number of entries, and high prediction power (correct classifications at the terminal nodes). In some embodiments, CART may be used in conjunction with a gradient-boosting algorithm, where each boosted tree is combined with its mates using a weighted voting scheme. Gradient boosting may be used to force the binary decision tree to classify data that was previously misclassified.

As noted above, a wide variety of statistical analysis techniques may be used to determine the one or more statistical relationships. These may include: one or more supervised learning techniques, one or more unsupervised learning techniques, one or more parametric analysis techniques (such as a Pearson's product-moment correlation coefficient r or an inner product), and/or one or more non-parametric analysis techniques. Non-parametric analysis techniques may include: a Wilcoxon matched pairs signed-rank test (for ordinal or ranked data), a Kolmogorov-Smirnov one-sample test (for ordinal or ranked data), a dependent t-test (for interval or ratio data), a Pearson chi-square, a chi-square test with a continuity correction (such as Yate's chi-square), a Mantel Heanszel chi-square test, a linear-by-linear association test, a maximum likelihood test, a risk ratio, an odds ratio, a log odds ratio, a Yule Q, a Yule Y, a phi-square, a Kappa measure of agreement, a McNemar change test, a Mann Whitney U-test, a Spearman's rank order correlation coefficient, a Kendall's rank correlation, a Krushcal-Wallis One-Way Analysis of Variance, and/or a Turkey's quick test.

Supervised learning techniques may include: least-squares regression (including correlation), ridge regression, partial least-squares (also referred to as partial correlation), a perceptron algorithm, a Winnow algorithm, linear discriminant analysis (LDA), Fisher discriminant analysis (FDA), logistic regression (LR), a Parzen windows classifier, a (k–) nearest-neighbor classification, multivariate adaptive regression splines (MARS), multiple additive regression trees (MART), SVM, LASSO (a regularized linear regression technique like ridge regression, but with $L_1$-norm regularization of the coefficients), least angle regression (LARS), decision trees (such as CART, with and without gradient boosting, such as ID3 and C4.5), bagging, boosting (such as, adaboost) of simple classifiers, kernel density classification, a minimax probability machine (MPM), multi-class classification, multi-label classification, a Gaussian Process classification and regression, Bayesian statistical analysis, a Naive Bayes classifier, and/or neural networks for regression and classification. While some of these supervised learning algorithms are linear, it should be understood that one or more additional non-linear versions may be derived using the same 'kernel-methodology', as previously described for the SVM, leading to a spectrum of kernel-based learning methods, for example, kernel FDA, kernelized logistic regression, the kernelized perceptron algorithm, etc. One or more of these non-linear versions may be used to perform the statistical analysis.

Unsupervised learning techniques may include: a kernel density estimation (using, for example, Parzen windows or k-nearest neighbors), more general density estimation techniques, quantile estimation, clustering, spectral clustering, k-means clustering, Gaussian mixture models, an algorithm using hierarchical clustering, dimensionality reduction, principal component analysis (PCA), multi-dimensional scaling (MDS), isomap, local linear embedding (LLE), self-organizing maps (SOM), novelty detection (which is also referred to as single-class classification, such as single-class SVM or single-class MPM), canonical correlation analysis (CCA), independent component analysis (ICA), factor analysis, and/or non-parametric Bayesian techniques like Dirichlet processes. As noted above for the supervised learning techniques, one or more additional non-linear versions of one or more linear unsupervised learning techniques may be used to perform the statistical analysis, such as kernel PCA, kernel CCA and/or kernel ICA.

In some embodiments, at least a portion of the statistical analysis, such as determination of one or more statistical relationships and/or identification of one or more association variables includes spectral analysis. For example, a Fourier transform or a discrete Fourier transform may be performed on the neural-activity information, one or more patterns of occurrence of one or more electrical signals, and/or one or more patterns of occurrence of one or more compound variables. Analysis in the frequency domain may allow patterns in at least some of the data to be determined.

In some embodiments, calculating one or more statistical relationships and/or identifying one or more association variables includes the use of design of experiments. For example, the data may correspond to an orthogonal array.

In some embodiments, a signal-to-noise metric is used to adjust how the one or more association variables are identified. This signal-to-noise metric may be computed using the set of electrical signals. Based on the computed signal-to-noise metric, how the one or more association variables are identified may vary from only using the occurrence and/or interaction rankings (for low values of the signal-to-noise metric) to only using the largest values of statistical association (e.g., without the occurrence and/or interaction rankings), which may be appropriate for high values of the signal-to-noise metric. In general, for an arbitrary value of the signal-to-noise metric, the one or more association variables may be identified using a weighted combination of the occurrence and/or interaction rankings and the largest values of statistical association, where the weights $\lambda_i$ of these terms may be a function of the signal-to-noise metric (for example, the weights of the two terms may be $\lambda$ and $1-\lambda$). Alternatively or additionally, such as weighted combination may be used in a modified version of a supervised learning technique, such as LASSO.

In some embodiments, the initial set of electrical signals is pruned or reduced prior to identifying the one or more association variables based on known or pre-determined association variables for the neural activity, such as one or more neurons or locations in the central nervous system that have been identified.

We now describe embodiments of a circuit and a computer system that may perform at least a portion of the statistical analysis and/or the identifying of the one or more association variables. This circuit may contain one or more filters, including: analog filters, digital filters, adaptive filters (using, for example, a least-square error or gradient approach, such as steepest decent), and/or neural networks. The one or more filters may be implemented using one or more digital signal processors (DSPs). In some embodiments, the statistical analysis and/or the identifying of the one or more association variables are implemented in hardware, for example, using one or more application-specific integrated circuits (ASICs), and/or using software.

Figure 6A:
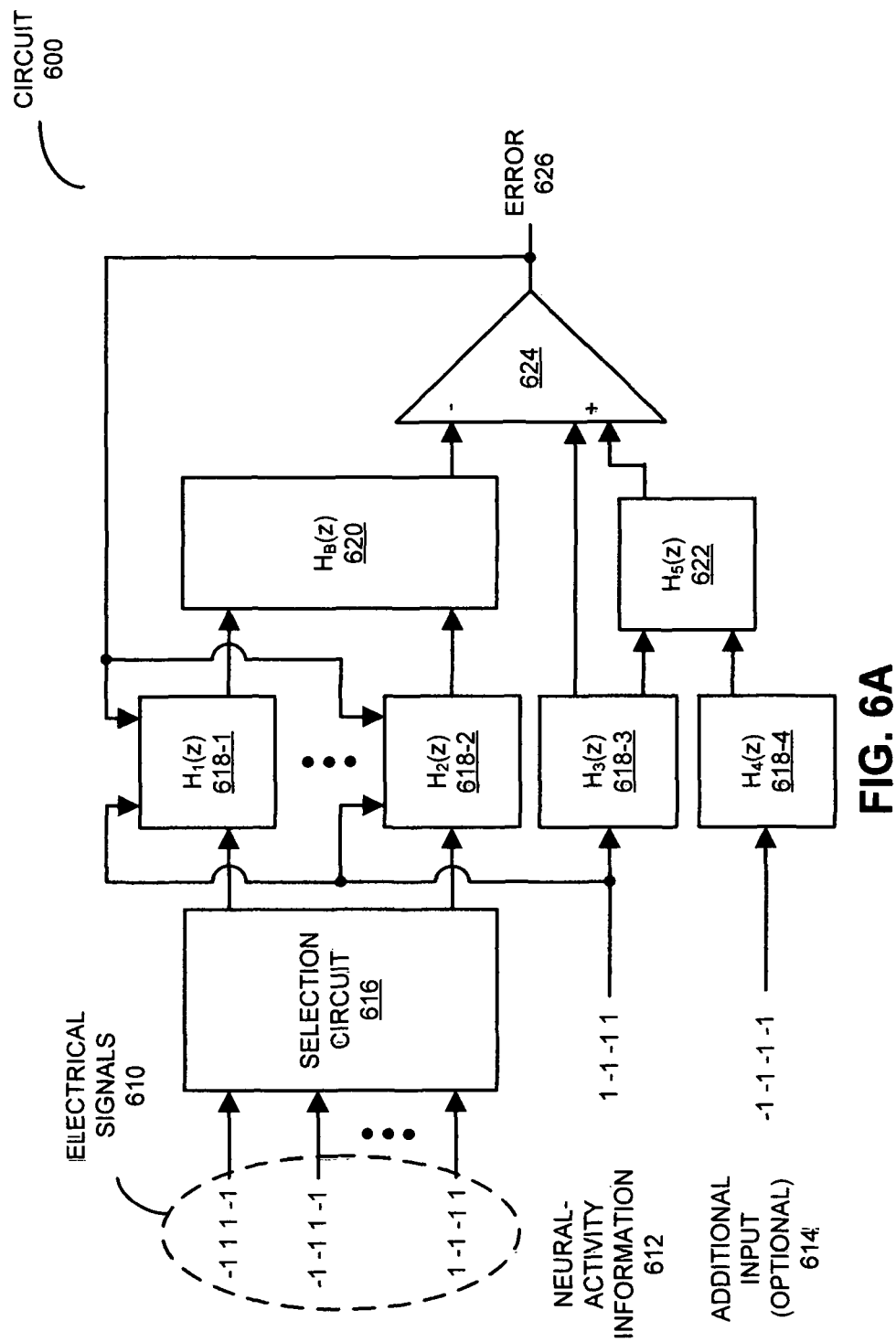
FIG. 6A is a block diagram illustrating a circuit in accordance with an embodiment of the present disclosure.

FIG. 6A presents a block diagram illustrating a circuit 600 for determining one or more statistical relationships and/or identifying one or more association variables. Presence (e.g., coded with 1s) and absence information (e.g., coded with −1s) for one or more electrical signals 610 are selectively coupled using selection circuit 616 to one or more filters $H_i$ 618. Note that the selection circuit 616 may be a multiplexer. In some embodiments, filters $H_i$ 618 perform spectral modification, such as limiting or excluding one or more of the electrical signals 610. Moreover, filters $H_i$ 618 may convert the presence and absence information for one or more of the electrical signals 610 into one or more patterns of occurrence.

Note that filters $H_i$ 618 may be adaptive. This adaptation may be based on neural-activity information 612 and/or an error 626. In some embodiments, the adaptation includes one or more time intervals and/or one or more offsets between these time intervals, which are used when determining compound variables (such as time intervals proximate to the occurrence of the neural activity). Note that the adaptation may minimize or reduce error 626 or a portion of error 626.

Outputs from one or more of the filters $H_i$ 618 may be coupled to filter $H_B$ 620. This filter may perform additional spectral modification. As a consequence, an arbitrary filtering operation may be implemented using one or more of the filters $H_i$ 618 and/or the filter $H_B$ 620. Moreover, filter $H_B$ 620 may determine a pattern of occurrence for one or more electrical signals 610 and/or one or more compound variables.

Neural-activity information 612 may be filtered using filter $H_3$ 618-3. Comparisons between an output of filter $H_3$ 618-3 and an output of the filter $H_B$ 620 may be performed using statistical analysis element 624. In some embodiments, statistical analysis element 624 may be a comparator. Statistical analysis element 624 may implement one or more statistical analysis techniques, such as the log-likelihood ratio or the odds ratio. Moreover, the statistical analysis element 624 may generate error 626. Note that error 626 may be: a scalar, a vector, and/or a matrix. In some embodiments, statistical analysis element 624 may perform a relative time shifting of the output of filter $H_3$ 618-3 and the output of filter $H_B$ 620.

In an exemplary embodiment, statistical analysis element 624 calculates one or more statistical relationships between the neural-activity information 612 and one or more patterns of occurrence of one or more compound variables. The one or more statistical relationships may be determined sequentially and/or substantially concurrently. Note that error 626 may correspond to the one or more statistical relationships.

In some embodiments, one or more optional additional inputs, such as optional additional input 614, is filtered using one or more filters, such as filter $H_4$ 618-4, and/or combined with neural-activity information 612 using a filter, such as filter/combiner $H_5$ 622. An output from filter/combiner $H_5$ 622 may be included in the analysis performed by statistical analysis element 624. The one or more optional additional inputs may allow inclusion of cross-terms. In some embodiments, the one or more optional additional inputs may include other variables (such as genetic information and/or environmental factors).

While a single output is shown for the filter $H_B$ 620, there may be additional outputs that are used by statistical analysis element 624. Similarly, there may be additional outputs from filter/combiner $H_5$ 622 that are used by statistical analysis element 624. While embodiment 600 uses presence and absence information in the one or more electrical signals 610, neural-activity information 612, and optional additional input 614, in some embodiments one or more of these items may only use presence information or may use only absence information.

Figure 6B:
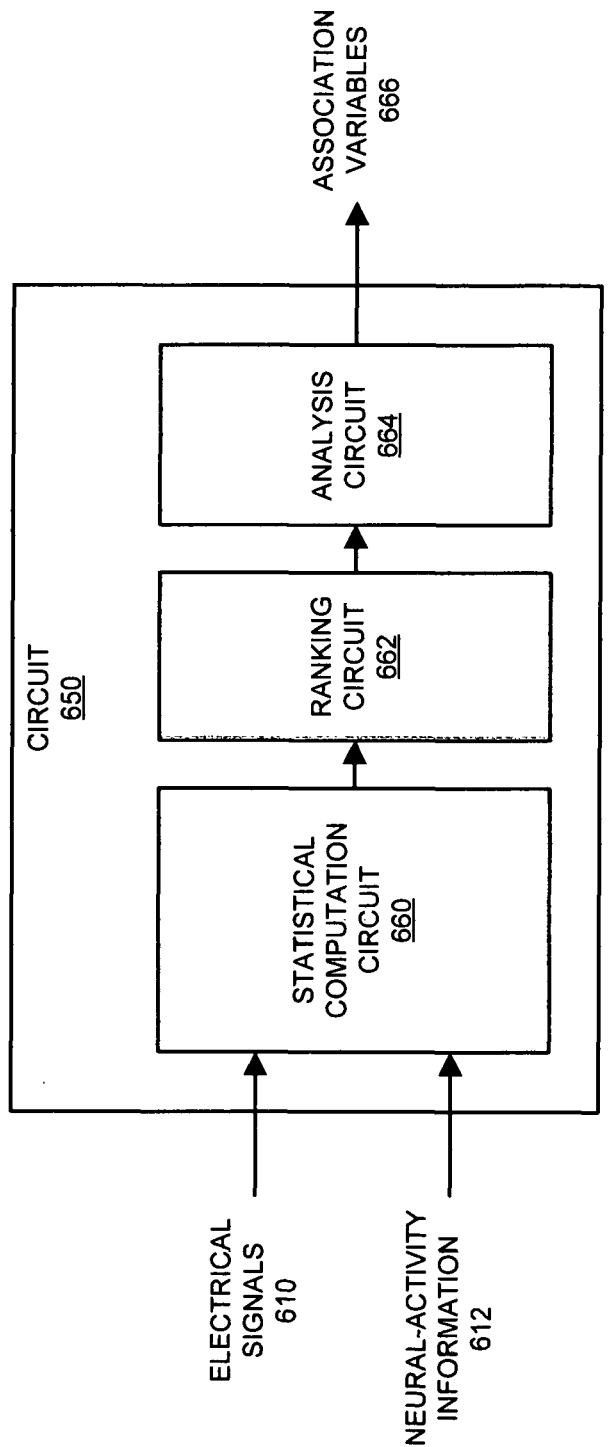
FIG. 6B is a block diagram illustrating a circuit in accordance with an embodiment of the present disclosure.

A more general description of a circuit to identify the one or more association variables is shown in FIG. 6B, which presents a block diagram illustrating circuit 650. In this circuit, electrical signals 610 and neural-activity information 612 are received by statistical computation circuit 660, which calculates the statistical relationships. (In some embodiments, one or more optional additional inputs, such as optional additional input 614 in FIG. 6A, are also received and used in the analysis.) Then, ranking circuit 662 determines the occurrence ranking of the number of occurrences of the electrical signals 610 in the subset of the compound variables and/or the numbers of different mathematical interactions used to determine the compound variables in the subset of the compound variables for electrical signals 610 that are associated with the corresponding numbers of occurrences, and analysis circuit 664 identifies the one or more association variables 666 based on the rankings (such as portion 518 in FIG. 5A which is substantially or approximately stable).

Circuits 600 (FIG. 6A) and 650 may include fewer components or additional components. Moreover, two or more components may be combined into a single component and/or a position of one or more components may be changed. In some embodiments the functionality of circuits 600 (FIG. 6A) and 650 is implemented more in hardware and less in software, or less in hardware and more in software, as is known in the art.

Devices and circuits described herein may be implemented using computer-aided design tools available in the art, and embodied by computer-readable files containing software descriptions of such circuits. These software descriptions may be: behavioral, register transfer, logic component, transistor and/or layout geometry-level descriptions. Moreover, the software descriptions may be stored on non-transitory computer-readable storage media.

Data formats in which such descriptions may be implemented include, but are not limited to: formats supporting behavioral languages like C, formats supporting register transfer level (RTL) languages like Verilog and VHDL, formats supporting geometry description languages (such as GDSII, GDSIII, GDSIV, CIF, and MEBES), and other suitable formats and languages. Note that physical files may be implemented on machine-readable media such as: 4 mm magnetic tape, 8 mm magnetic tape, 3½ inch floppy media, CDs, DVDs, and so on.

FIG. 7 presents a block diagram illustrating a computer system 700. Computer system 700 includes: one or more processors (or processor cores) 710, a communication interface 712, a user interface 714, and one or more signal lines 722 coupling these components together. Note that the one or more processors (or processor cores) 710 may support parallel processing and/or multi-threaded operation, communication interface 712 may have a persistent communication connection, and the one or more signal lines 722 may constitute a communication bus. Moreover, user interface 714 may include: a display 716, a keyboard 718, and/or a pointer 720, such as a mouse.

Memory 724 in computer system 700 may include volatile memory and/or non-volatile memory. More specifically, memory 724 may include: ROM, RAM, EPROM, EEPROM, flash, one or more smart cards, one or more magnetic disc storage devices, and/or one or more optical storage devices. Memory 724 may store an operating system 726 that includes procedures (or a set of instructions) for handling various basic system services for performing hardware-dependent tasks. Moreover, memory 724 may also store communication procedures (or a set of instructions) in a communication module 728. These communication procedures may be used for communicating with one or more computers, devices and/or servers, including computers, devices and/or servers that are remotely located with respect to computer system 700.

Memory 724 may also include one or more program modules 730, including: statistical analysis module 730 (or a set of instructions), conversion module 732 (or a set of instructions), ranking module 734 (or a set of instructions), background-correction module 736 (or a set of instructions), compound-variable generator 742 (or a set of instructions), optional signal-processing module 746 (or a set of instructions), and/or sequence generator 750 (or a set of instructions). Note that one or more of these program modules (or sets of instructions) may constitute a computer-program mechanism.

Conversion module 732 may convert electrical signals 738 for one or more organisms, such as electrical signal A 740-1 or electrical signal B 740-2, into categorical data. In some embodiments, electrical signals 738 and/or information for one or more neural activities 752 associated with the one or more organisms are preconditioned using optional signal-processing module 746. For example, optional signal-processing module 746 may filter data and/or may perform a transform, such as: a fast Fourier transform, a Laplace transform, a discrete Fourier transform, a Z-transform, and/or any other transform technique now known or later developed.

Then, compound-variable generator 742 may determine one or more compound variables 754 using one or more mathematical interactions 758 and at least some of the electrical signals 738 (for example, statistical analysis module 730 may exclude one or more of the electrical signals 738 using optional correlation data 748). Alternatively, compound variables 754 may be pre-determined. Note that in some embodiments compound variables 754 are determined using optional weights 744.

Next, statistical analysis module 730 may determine statistical relationships between a pattern of occurrence of one or more neural activities 752 and patterns of occurrence of at least some of the compound variables 754. (Note that statistical analysis module 730 may exclude one or more of the compound variables 754 prior to determining the statistical relationships.) Moreover, ranking module 734 may determine one or more rankings 760 of the number of occurrences of electrical signals in statistically significant statistical compound variables above a noise floor. For example, the one or more rankings 760 may include one or more occurrence rankings at different statistical significance criteria and/or one or more interaction rankings.

Additionally, background-correction module 736 may determine another occurrence ranking based on statistical relationships between at least some of the compound variables 754 and a sequence of values generated using sequence generator 750. This other occurrence ranking may be subtracted from at least one of the occurrence rankings in one or more rankings 760.

Then, statistical analysis module 730 may identify one or more association variables 756 based on ranking 760 (which may include an occurrence ranking after correcting for the background). In some embodiments, the operations of the various modules are repeated to higher order, i.e., in compound variables that include additional electrical signals in the electrical signals 738.

Instructions in the various modules in the memory 724 may be implemented in: a high-level procedural language, an object-oriented programming language, and/or in an assembly or machine language. The programming language may be compiled or interpreted, i.e., configurable or configured, to be executed by the one or more processors (or processor cores) 710.

Although computer system 700 is illustrated as having a number of discrete components, FIG. 7 is intended to be a functional description of the various features that may be present in computer system 700 rather than a structural schematic of the embodiments described herein. In practice, and as recognized by those of ordinary skill in the art, the functions of computer system 700 may be distributed over a large number of servers or computers, with various groups of the servers or computers performing particular subsets of the functions. In some embodiments, some or all of the functionality of computer system 700 may be implemented in one or more ASICs and/or one or more DSPs.

Computer system 700 may include fewer components or additional components. Moreover, two or more components may be combined into a single component and/or a position of one or more components may be changed. In some embodiments the functionality of computer system 700 may be implemented more in hardware and less in software, or less in hardware and more in software, as is known in the art.

Figure 8:
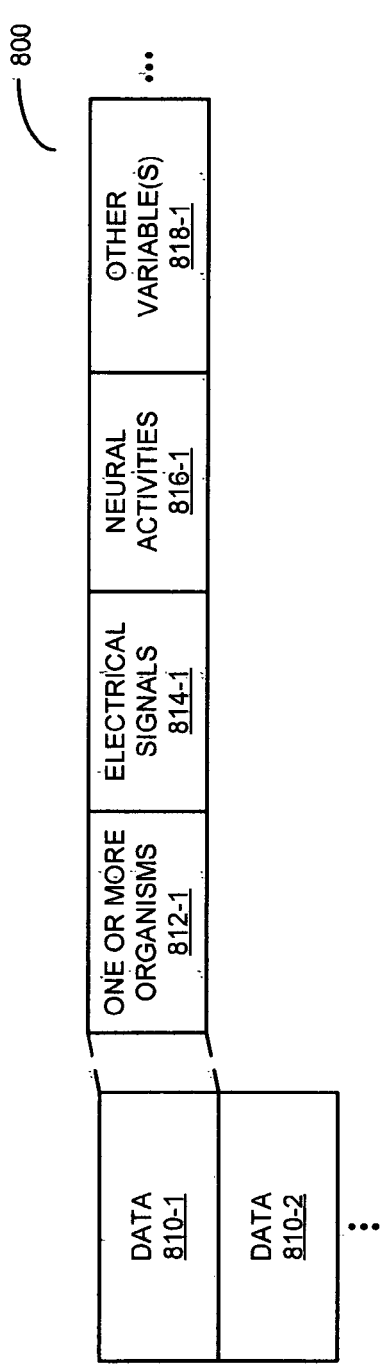
FIG. 8 is a block diagram illustrating a data structure in accordance with an embodiment of the present disclosure.

We now describe embodiments of a data structure that may be used in computer system 700. FIG. 8 presents a block diagram illustrating a data structure 800. This data structure may include information or data 810, such as electrical signals, compound variables, and/or neural-activity information associated with one or more organisms. For example, for data 810-1, the information may include: one or more organisms 812-1, one or more electrical signals 814-1 associated with the one or more organisms 812-1, information about one or more associated neural activities 816-1 of the one or more organisms 812-1, and/or one or more other variables 818-1 (which may be included with the one or more electrical signals 814-1).

Figure 9:
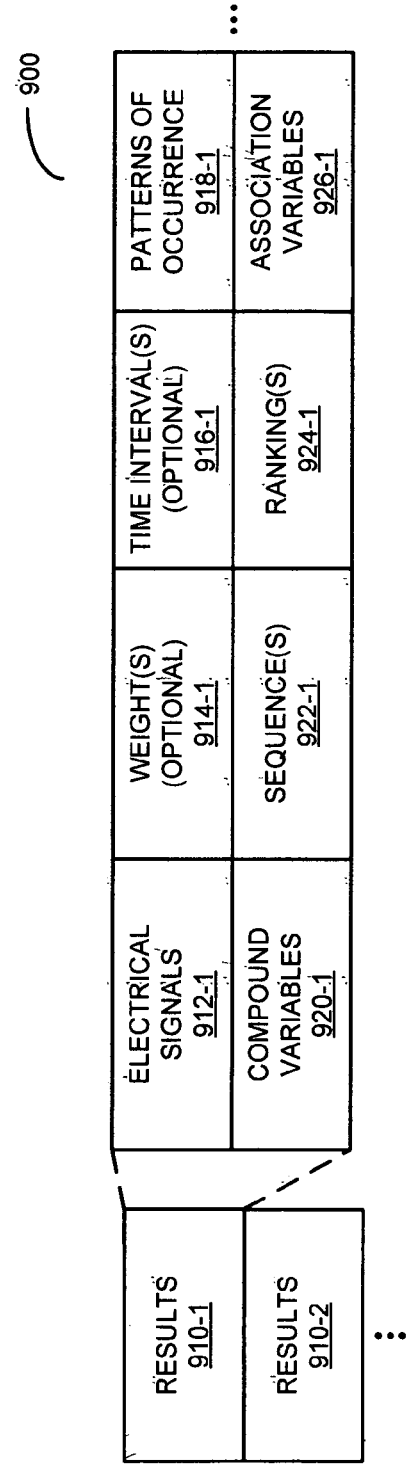
FIG. 9 is a block diagram illustrating a data structure in accordance with an embodiment of the present disclosure.

FIG. 9 presents a block diagram illustrating a data structure 900. This data structure may include results 910, such as statistical relationships, rankings, and/or association variables for one or more populations, such as the one or more organisms, and/or one or more subsets of a given population. For example, results 910-1 may include: one or more electrical signals 912-1, one or more optional weights 914-1, one or more optional time intervals 916-1, one or more patterns of occurrence 918-1, one or more compound variables 920-1, one or more sequences 922-1 (such as a sequence of random or pseudorandom values), one or more rankings 924-1 (such as one or more occurrence rankings and/or one or more interaction rankings), and/or one or more association variables 926-1.

Note that in some embodiments of the data structures 800 (FIG. 8) and/or 900 there may be fewer or additional components. Moreover, two or more components may be combined into a single component and/or a position of one or more components may be changed.

While embodiments of apparatuses and related methods for identifying one or more association variables have been described, the apparatuses and related methods may be applied generally to determine statistical relationships in a wide variety of underdetermined problems in medicine, psychology, statistics, engineering, finance, applied mathematics and operations research (and, thus, in general to an arbitrary supervised learning problem). Consequently, the one or more association variables may be identified based on neural activities or features other than those corresponding to electrical signals, such as physiological measurements (for example, pulse, temperature, acceleration, etc.). Alternatively or additionally, the analysis technique may be applied to signals other than electrical signals that are associated with neural activity, such as optical signals and/or magnetic signals (for example, data obtained using magnetoencephalography).

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Thus, the present disclosure is not intended to be limited to the embodiments shown, but is to be accorded the widest scope consistent with the principles and features disclosed herein.

What is claimed:

1. A computer system, comprising:
   one or more computation devices, wherein the one or more computation devices comprise one or more of: a processor, one or more cores in a second processor, or another type of device configured for computation;
   memory configured to store a program module, wherein, when executed by the one or more computation devices, the program module causes the computer system to perform one or more operations comprising:
   accessing a stored set of electrical signals, which are associated with corresponding electrodes and which are measured for an organism, and an associated pattern of occurrence of a neural activity in the organism;

determining patterns of occurrence of combinations of the set of electrical signals based on the set of electrical signals and a set of mathematical interactions, a pattern of occurrence of a combination corresponding to patterns of occurrence of at least a pair of electrical signals for the organism and a mathematical interaction;

calculating statistical associations between the patterns of occurrence of the combinations and a pattern of occurrence of the neural activity for the organism, a statistical association corresponding to the pattern of occurrence of the combination and the pattern of occurrence of the neural activity;

performing second operations at different statistical-association threshold values until a noise-floor criterion is valid, wherein the second operations comprise:

selecting a given subset of the combinations having statistical associations that are larger than a given statistical-association threshold value;

determining one or more given aggregate properties of the given subset of the combinations, wherein the one or more given aggregate properties comprise given numbers of occurrences of the electrical signals in the given subset of the combinations;

computing a given ranking of the electrical signals based on the determined one or more given aggregate properties; and assessing whether the noise-floor criterion is valid by comparing the given ranking to at least another ranking of the electrical signals based on another instance of the one or more aggregate properties corresponding to another statistical-association threshold value to determine whether at least a portion of the given ranking and the other ranking are approximately stable; and identifying a subset of electrical signals in the set of electrical signals based on one or more final aggregate properties of at least a final subset of the combinations corresponding to at least a final statistical-association threshold value where the stability criterion is valid, wherein the one or more final aggregate properties comprise numbers of occurrences of the electrical signals in the at least the final subset of the combinations.

2. The computer system of claim 1, wherein the one or more operations comprise providing a predictive model based at least on the subset of electrical signals, the pattern of neural activity and a supervised-learning technique; and wherein the predictive model provides a value for a therapeutic intervention for an individual based on at least some of the subset of electrical signals.

3. The computer system of claim 2, wherein the supervised-learning technique comprises at least one of: a kernel method, a least absolute shrinkage and selection operator (LASSO), logistic regression, ridge regression, a regression technique, a classification technique, a Bayesian technique, or a neural network.

4. The computer system of claim 1, wherein the set of mathematical operations comprise nonlinear mathematical operations.

5. The computer system of claim 1, wherein the one or more final aggregate properties comprise numbers of occurrences of mathematical operations in the set of mathematical operations in the combinations in the final subset of the combinations.

6. The computer system of claim 1, wherein the second operations identify a noise floor associated with the combinations.

7. The computer system of claim 1, wherein the set of electrical signals correspond to one of: brainwave data, or neurological stimulation.

8. The computer system of claim 1, wherein the subset of electrical signals have p-values that are statistically significant based on a statistical criterion.

9. The computer system of claim 8, wherein the p-values include a Bonferroni correction that is based on the number of combinations.

10. A non-transitory computer-readable storage medium for use in conjunction with a computer system, the computer-readable storage medium storing a program module, wherein, when executed by the computer system, the program module causes the computer system to perform one or more operations comprising:

accessing a stored set of electrical signals, which are associated with corresponding electrodes and which are measured for an organism, and an associated pattern of occurrence of a neural activity in the organism;

determining patterns of occurrence of combinations of the set of electrical signals based on the set of electrical signals and a set of mathematical interactions, a pattern of occurrence of a combination corresponding to patterns of occurrence of at least a pair of electrical signals for the organism and a mathematical interaction;

calculating statistical associations between the patterns of occurrence of the combinations and a pattern of occurrence of the neural activity for the organism, a statistical association corresponding to the pattern of occurrence of the combination and the pattern of occurrence of the neural activity;

performing second operations at different statistical-association threshold values until a noise-floor criterion is valid, wherein the second operations comprise:

selecting a given subset of the combinations having statistical associations that are larger than a given statistical-association threshold value;

determining one or more given aggregate properties of the given subset of the combinations, wherein the one or more given aggregate properties comprise given numbers of occurrences of the electrical signals in the given subset of the combinations;

computing a given ranking of the electrical signals based on the determined one or more given aggregate properties; and assessing whether the noise-floor criterion is valid by comparing the given ranking to at least another ranking of the electrical signals based on another instance of the one or more aggregate properties corresponding to another statistical-association threshold value to determine whether at least a portion of the given ranking and the other ranking are approximately stable; and identifying a subset of electrical signals in the set of electrical signals based on one or more final aggregate properties of at least a final subset of the combinations corresponding to at least a final statistical-association threshold value where the stability criterion is valid, wherein the one or more final aggregate properties comprise numbers of occurrences of the electrical signals in the at least the final subset of the combinations.

11. The computer-readable storage medium of claim 10, wherein the one or more operations comprise providing a predictive model based at least on the subset of electrical signals, the pattern of neural activity and a supervised-learning technique; and wherein the predictive model provides a value for a therapeutic intervention for an individual based on at least some of the subset of electrical signals.

12. The computer-readable storage medium of claim 10, wherein the one or more final aggregate properties comprise numbers of occurrences of mathematical operations in the set of mathematical operations in the combinations in the final subset of the combinations.

13. The computer-readable storage medium of claim 10, wherein the second operations identify a noise floor associated with the combinations.

14. The computer-readable storage medium of claim 10, wherein the set of electrical signals correspond to one of: brainwave data, or neurological stimulation.

15. The computer-readable storage medium of claim 10, wherein the subset of electrical signals have p-values that are statistically significant based on a statistical criterion.

16. The computer-readable storage medium of claim 15, wherein the p-values include a Bonferroni correction that is based on the number of combinations.

17. A method for identifying a subset of electrical signals, comprising:

by a program module executed by a computer system:
accessing a stored set of electrical signals, which are associated with corresponding electrodes and which are measured for an organism, and an associated pattern of occurrence of a neural activity in the organism;

determining patterns of occurrence of combinations of the set of electrical signals based on the set of electrical signals and a set of mathematical interactions, a pattern of occurrence of a combination corresponding to patterns of occurrence of at least a pair of electrical signals for the organism and a mathematical interaction;

calculating statistical associations between the patterns of occurrence of the combinations and a pattern of occurrence of the neural activity for the organism, a statistical association corresponding to the pattern of occurrence of the combination and the pattern of occurrence of the neural activity;

performing second operations at different statistical-association threshold values until a noise-floor criterion is valid, wherein the second operations comprise:

selecting a given subset of the combinations having statistical associations that are larger than a given statistical-association threshold value;

determining one or more given aggregate properties of the given subset of the combinations, wherein the one or more given aggregate properties comprise given numbers of occurrences of the electrical signals in the given subset of the combinations;

computing a given ranking of the electrical signals based on the determined one or more given aggregate properties; and assessing whether the noise-floor criterion is valid by comparing the given ranking to at least another ranking of the electrical signals based on another instance of the one or more aggregate properties corresponding to another statistical-association threshold value to determine whether at least a portion of the given ranking and the other ranking are approximately stable; and identifying the subset of electrical signals in the set of electrical signals based on one or more final aggregate properties of at least a final subset of the combinations corresponding to at least a final statistical-association threshold value where the stability criterion is valid, wherein the one or more final aggregate properties comprise numbers of occurrences of the electrical signals in the at least the final subset of the combinations.

18. The method of claim 17, wherein the method comprises providing a predictive model based at least on the subset of electrical signals, the pattern of occurrence of the neural activity and a supervised-learning technique; and wherein the predictive model provides a value for a therapeutic intervention for an individual based on at least some of the subset of electrical signals.

19. The method of claim 17, wherein the one or more final aggregate properties comprise numbers of occurrences of mathematical operations in the set of mathematical operations in the combinations in the final subset of the combinations.

20. The method of claim 17, wherein the second operations identify a noise floor associated with the combinations.

21. The method of claim 17, wherein the set of electrical signals correspond to one of: brainwave data, or neurological stimulation.

22. The method of claim 17, wherein the subset of electrical signals have p-values that are statistically significant based on a statistical criterion.

23. The method of claim 22, wherein the p-values include a Bonferroni correction that is based on the number of combinations.

* * * * *